(12) United States Patent
Chen et al.

(10) Patent No.: US 8,454,513 B2
(45) Date of Patent: Jun. 4, 2013

(54) MICRO-MACHINED MEDICAL DEVICES, METHODS OF FABRICATING MICRODEVICES, AND METHODS OF MEDICAL DIAGNOSIS, IMAGING, STIMULATION, AND TREATMENT

(75) Inventors: Jingkuang Chen, Albuquerque, NM (US); Xiaoyang Cheng, Ann Arbor, MI (US)

(73) Assignee: STC.UNM, Albuquerque, NM (US)

( * ) Notice: Subject to any disclaimer, the term of this patent is extended or adjusted under 35 U.S.C. 154(b) by 1242 days.

(21) Appl. No.: 11/320,921

(22) Filed: Dec. 30, 2005

(65) Prior Publication Data

US 2006/0163680 A1 Jul. 27, 2006

Related U.S. Application Data

(60) Provisional application No. 60/640,601, filed on Dec. 30, 2004, provisional application No. 60/734,385, filed on Nov. 8, 2005, provisional application No. 60/739,942, filed on Nov. 28, 2005.

(51) Int. Cl.
*A61B 1/12* (2006.01)

(52) U.S. Cl.
USPC .......... 600/439; 600/459; 600/462; 600/471; 257/416

(58) Field of Classification Search
USPC .................. 257/416; 600/407–480
See application file for complete search history.

(56) References Cited

U.S. PATENT DOCUMENTS

| | | | | | |
|---|---|---|---|---|---|
| 3,332,807 | A | * | 7/1967 | Boehmer et al. | 136/203 |
| 5,837,929 | A | * | 11/1998 | Adelman | 136/225 |
| 6,046,398 | A | * | 4/2000 | Foote et al. | 136/201 |
| 6,136,212 | A | * | 10/2000 | Mastrangelo et al. | 216/49 |
| 6,136,630 | A | * | 10/2000 | Weigold et al. | 438/50 |
| 6,379,325 | B1 | * | 4/2002 | Benett et al. | 604/22 |
| 6,582,987 | B2 | * | 6/2003 | Jun et al. | 438/49 |
| 6,812,563 | B2 | * | 11/2004 | Go et al. | 257/715 |
| 7,063,798 | B2 | * | 6/2006 | D'arrigo Guiseppe et al. | 216/67 |
| 2001/0007940 | A1 | * | 7/2001 | Tu et al. | 606/41 |
| 2002/0063330 | A1 | * | 5/2002 | Macris | 257/712 |
| 2003/0209534 | A1 | * | 11/2003 | Ferguson | 219/548 |
| 2005/0064581 | A1 | * | 3/2005 | Manalis et al. | 435/287.2 |
| 2006/0004289 | A1 | * | 1/2006 | Tian et al. | 600/459 |
| 2006/0084875 | A1 | * | 4/2006 | Knight | 600/462 |

\* cited by examiner

*Primary Examiner* — Tse Chen
*Assistant Examiner* — Vani Gupta
(74) *Attorney, Agent, or Firm* — Schwegman Lundberg & Woessner, P.A.

(57) ABSTRACT

A medical device may include a micro-machined substrate, at least one thermo-electric assembly associated with the substrate, and a cooling system configured to configured to remove heat from the a region of the substrate proximal the substrate. According to various aspects, a method of clearing plaque from a blood vessel may include implanting a micro-device in the blood vessel, wherein the micro-device may include at least one ultrasonic transducer, and operably controlling the micro-device to emit high frequency ultrasonic waves for breaking up said plaque.

20 Claims, 16 Drawing Sheets

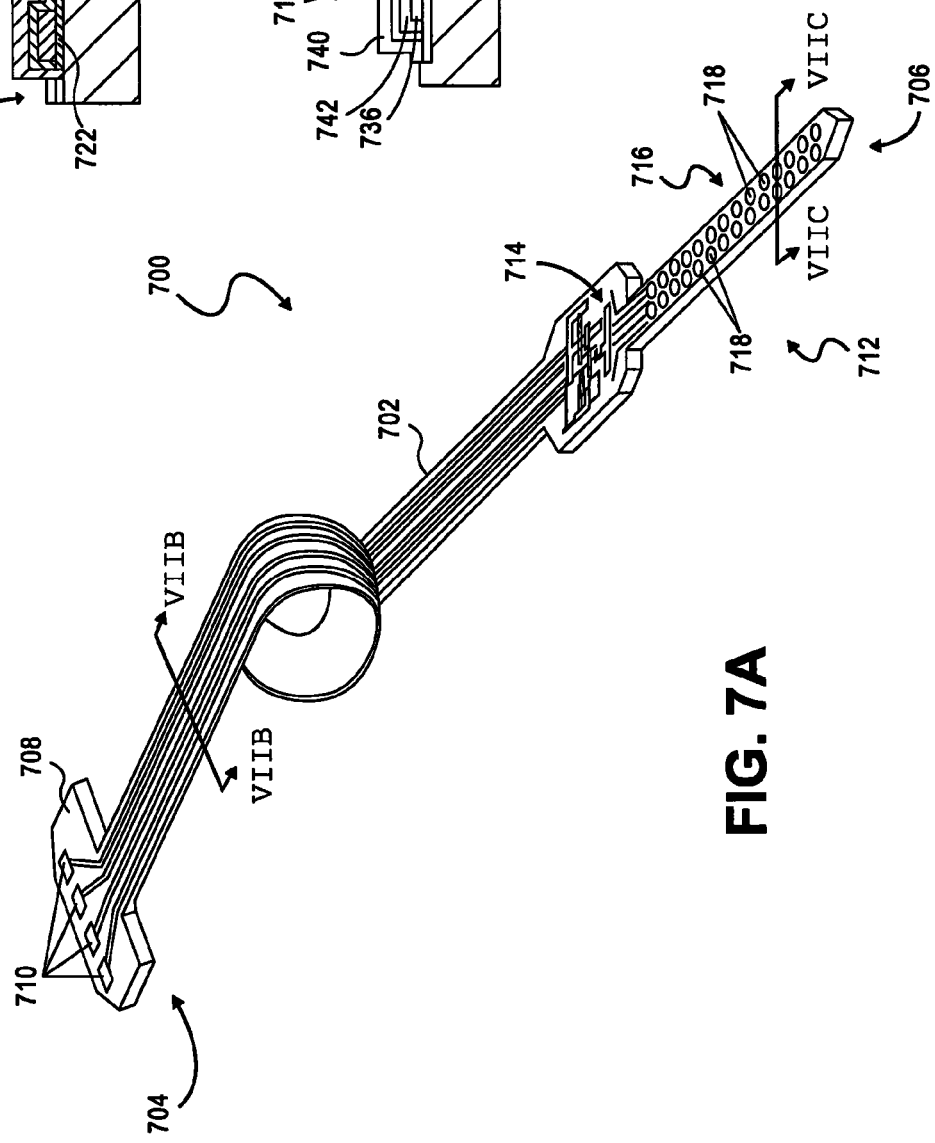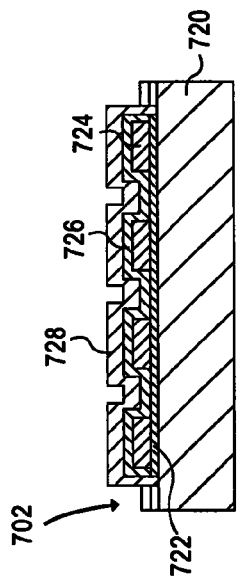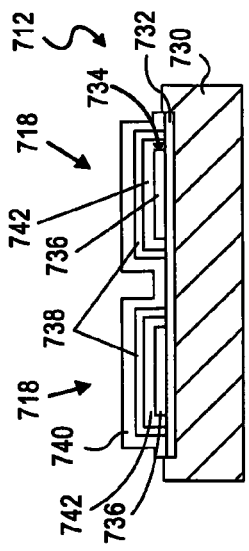
FIG. 7B
FIG. 7C
FIG. 7A

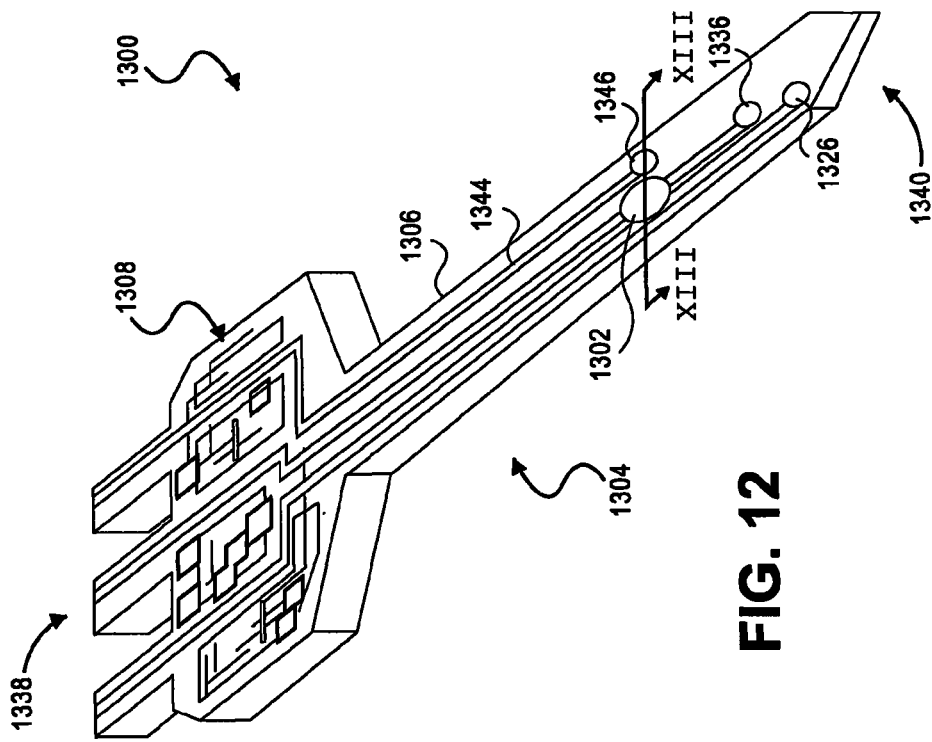
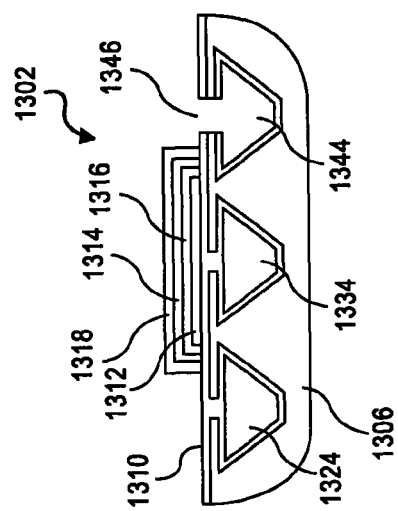
FIG. 12
FIG. 13

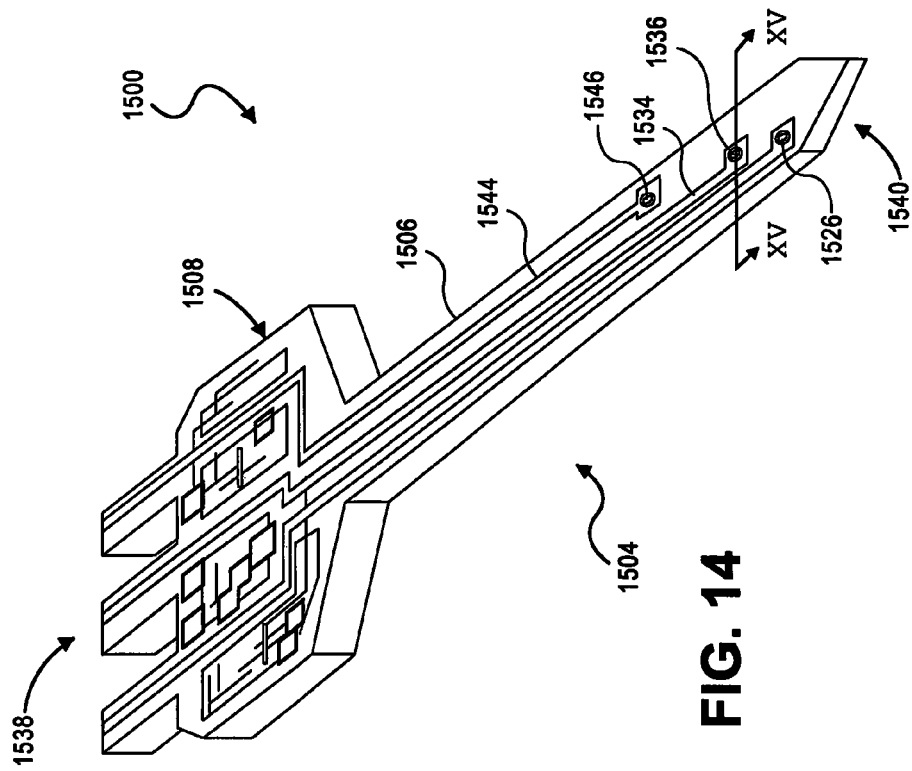
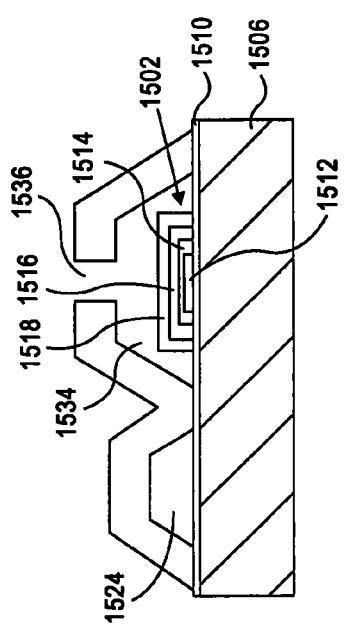
FIG. 14
FIG. 15

MICRO-MACHINED MEDICAL DEVICES, METHODS OF FABRICATING MICRODEVICES, AND METHODS OF MEDICAL DIAGNOSIS, IMAGING, STIMULATION, AND TREATMENT

CROSS-REFERENCE TO RELATED APPLICATIONS

This application claims the benefit of priority of U.S. provisional application No. 60/640,601, filed on Dec. 30, 2004, U.S. provisional patent application No. 60/734,385 entitled "Silicon Implantable Transducer Systems for Medical Applications," filed on Nov. 8, 2005, and U.S. provisional application No. 60/739,942, filed on Nov, 28, 2005, the contents of all of which are incorporated herein by reference in their entirety.

TECHNICAL FIELD

The present disclosure is directed generally to medical devices and methods. More particularly, the present disclosure is directed to micro-machined medical devices, methods of fabricating micro devices, and methods of medical diagnosis, imaging, stimulation, and treatment.

BACKGROUND

Conventional ultrasound devices may be used for medical diagnosis, imaging, and stimulation. For example, ultrasound imaging generally involves transmission of high frequency sound into the body followed by the reception, processing, and parametric display of echoes returning from structures and tissues within the body. In addition, ultrasounds can be used to heat tissue, change cell membrane permeability, and enhance healing speed of a wound or bone fracture. Also, by measuring the echoes of ultrasounds bouncing back from a blood flow, the blood flow rate can be determined. By measuring the propagation speed of ultrasounds in tissue, the tissue temperature can be identified.

Unfortunately, traditional medical ultrasonic systems are bulky and normally operate outside the body. Some conventional intravascular ultrasounds (IVUS) can be inserted through blood vessels for examining vessels in the body and the arteries in the heart. However, its size (typically 3-4 millimeters in diameter) limits its use to larger vessels.

Image resolution from conventional ultrasound systems is relatively poor, especially for anatomical structures deep inside body tissue. Because of wavelength related penetration depth limit, long-wavelength ultrasonic waves are required for detection and/or stimulation of organs/tissues. For imaging or diagnosis applications, long-wavelength acoustic waves limit the image resolution or the accuracy of the measurement/diagnosis. For therapeutic stimulation, long-wavelength ultrasounds generally spread over an area larger than needed and could negatively affect the neighboring healthy tissue.

Short-wavelength waves are capable of providing images of higher resolution. They also are easier to focus on the target tissue in diagnosis or stimulation applications. However, limited by their short penetration depth, they cannot penetrate through the body to reach a target deep inside the tissue.

Conventional cryoprobes (for introduction of liquid nitrogen to freeze tissue), temperature-sensing probes, and/or an ultrasound imaging device may be provided for performing a cryosurgery. The temperature sensor and the ultrasound imager may be used to monitor the temperature and anatomical structure of tissue during a freezing and thawing process. These conventional probes and devices are typically of millimeter to centimeter diameter cross-section and cause significant disruption to the tissue. They are not suitable for operation in more delicate organs, for example, the brain and liver, because the disruption (and as a result the damage) is too much.

Conventional approaches for micromachining a silicon substrate to form miniature implantable devices include the dissolving wafer process using boron etch-stop and the dry-etching micromachining on a silicon-on-insulator (SOI) wafer. The dissolving wafer process is typically able to accurately control the silicon substrate dimension to within $\pm 1$ μm and has been used to fabricate electrode arrays and multi-channel drug delivery chips. The drawback of the boron-defined dissolving wafer process comes from the diffusion process required for doping the silicon and the high tensile stress in the boron-doped silicon. The high-temperature boron diffusion process may not be very compatible with transistor and/or MEMS processes. Additionally, the boron-caused high-stress may warp the device structure. The SOI micromachining may utilize double-sided dry etching to form a probe-shaped silicon substrate on the silicon layer of a SOI structure. The device thickness is determined by the thickness of the SOI structure. The thick substrate under the buried oxide is removed by a backside deep silicon etching. While this approach may provide good control on the final device dimension and prevents the stress problem, it requires use of a high-cost SOI wafer.

The present disclosure describes exemplary embodiments of medical devices, fabrication methods, and medical procedures that may solve one or more of the above problems.

SUMMARY OF THE INVENTION

In various aspects, the present disclosure is directed to devices that may comprise a micro machined channel network integrated with at least one micro-thermoelectric device on a miniature silicon probe. According to some aspects, devices may comprise a temperature sensor integrated with a thermoelectric device and configured for bi-directional cell temperature control. In accordance with various aspects, devices configured to monitor anatomical structures of tissue during a cryosurgery may comprise a micro-electro-mechanical-system (MEMS) ultrasound imaging device integrated with a thermoelectric device. In some aspects, devices may comprise micro-thermoelectric devices integrated with a drug delivery channel network and an electrode array on a micro machined silicon probe and configured to control cell temperature, deliver drugs at the cellular level, and/or electrically stimulate and/or record cells and tissue.

In various aspects, the present disclosure is directed to methods of cell freezing and heating, which may comprise integrating a micro machined channel network with at least one micro-thermoelectric device on a miniature silicon probe. According to some aspects, methods of bi-directionally controlling cell temperature may comprise integrating a temperature sensor with a thermoelectric device. In accordance with various aspects, methods of monitoring anatomical structures of tissue during a cryosurgery may comprise integrating a micro-electro-mechanical-system (MEMS) ultrasound imaging device with a thermoelectric device. In some aspects, methods of controlling cell temperature, methods of cellular level drug delivery, and/or methods of electrical stimulation/recording of cells and tissue may comprise integrating micro-thermoelectric devices with a drug delivery channel network and an electrode array on a micro machined silicon probe.

In some aspects, the present disclosure is directed to methods of fabricating one or more of the medical devices disclosed herein, including, for example, adding a self-aligned silicon dioxide layer under a first polysilicon layer to minimize the charge buildup associated with a silicon nitride-polysilicon interface.

In accordance with some aspects, a medical device may include a micro-machined substrate, at least one thermoelectric assembly associated with the substrate, and a cooling system configured to configured to remove heat from the a region of the substrate proximal the substrate.

According to some aspects, a medical device may comprise a micro-machined substrate, at least one thermo-electric assembly associated with the substrate, an electronics assembly configured to control the thermoelectric assembly, and a temperature sensor. The sensor may cooperate with the electronics assembly to provide bi-directional temperature control of the thermo-electric assembly.

In accordance with some aspects, a medical device may comprise a micro-machined substrate and at least one transducer associated with the substrate. The transducer may be configured to send and receive ultrasonic waves According to various aspects, a method of clearing plaque from a blood vessel may include implanting a micro-device in the blood vessel, wherein the micro-device may include at least one ultrasonic transducer, and operably controlling the micro-device to emit high frequency ultrasonic waves for breaking up said plaque.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate several exemplary embodiments of the invention and, together with the description, serve to explain the principles of the invention. In the drawings.

FIG. 7A is a perspective view of an exemplary medical device in accordance with various aspects of the disclosure;

FIG. 7B is a cross-sectional view along line VIIB-VIIB of FIG. 7A;

FIG. 7C is a cross-sectional view along line VIIC-VIIC of FIG. 7A;

FIG. 12 shows an example medical device in accordance with various aspects of the disclosure;

FIG. 13 shows a cross-sectional view including an example transducer associated with the example medical device of FIG. 12 in accordance with various aspects of the disclosure;

FIG. 14 shows an example medical device in accordance with various aspects of the disclosure; and FIG. 15 shows a cross-sectional view including an example transducer associated with the example medical device of FIG. 14 in accordance with various aspects of the disclosure.

DETAILED DESCRIPTION

Reference will now be made in detail to embodiments of the invention, examples of which are illustrated in the accompanying drawings. Wherever possible, the same reference numbers will be used throughout the drawings to refer to the same or like parts.

Figure 1:
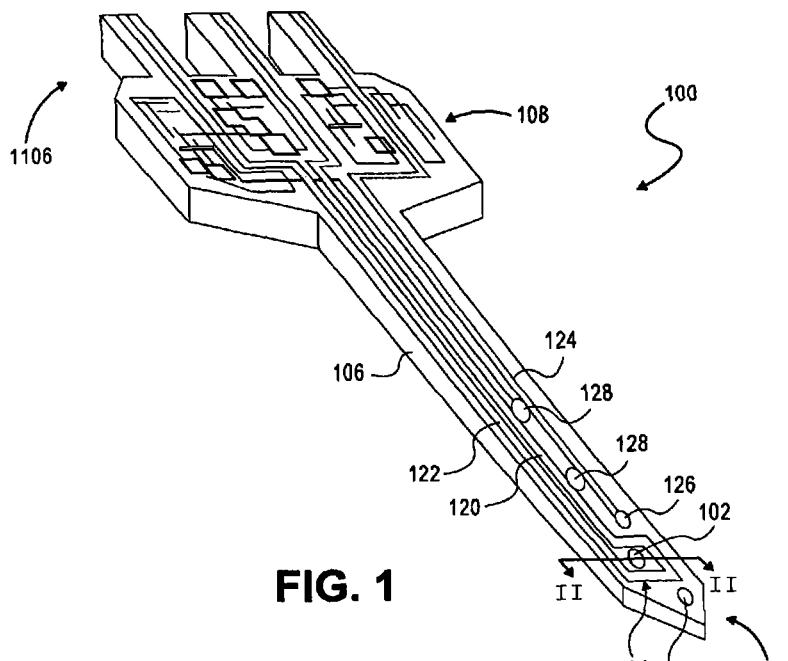
FIG. 1 is a perspective view of an exemplary medical device in accordance with various aspects of the disclosure.
Figure 2:
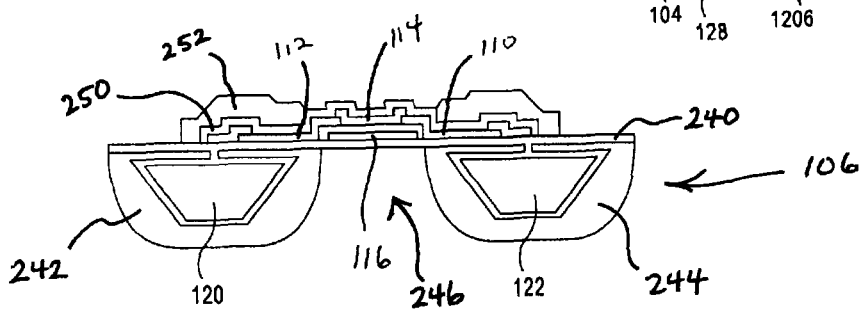
FIG. 2 is a cross-sectional view along line II-II of FIG. 1.

Referring to FIGS. 1 and 2, an exemplary embodiment of the present invention will be described. FIG. 1 illustrates an exemplary medical device 100 in accordance with various aspects of the invention. The medical device 100 may comprise a thermoelectric assembly 102 and a cooling system 104 associated with a substrate 106, for example, a micro-machined substrate. The substrate 106 may comprise, for example, silicon, silicon germanium, or any other know substrate. The substrate may have a first end 1106 sized and configured for connection to at least one fluid conduit, for example, a pipette, and a second end 1206 sized and configured for insertion into a body tissue, for example, a human body tissue such as, for example, arteries, organs, or the like, including delicate organs such as the brain and the liver. The second end 1206 may be at an opposite end of the substrate 106 relative to the first end 1106.

As shown in FIG. 2, the thermoelectric assembly 102 may comprise an n-type semiconductor 110, a p-type semiconductor 112, and a metal interconnect 114 electrically coupling the semiconductors 110, 112 with one another to thereby form a semiconductor-metal junction. The n-type semiconductor 110 may comprise, for example, silicon, silicon germanium, or any known semiconductor doped with boron or any known dopant, and the p-type semiconductor 112 may comprise silicon, silicon germanium, or any known semiconductor doped with boron or any known dopant. The metal interconnect 114 may comprise, for example, aluminum.

A thermistor 116, for example, a semiconductor thermistor, may be disposed proximal the thermoelectric assembly 102 to monitor the temperature of the device 100. The thermistor 116 may comprise, for example, a polysilicon thermistor.

The device 100 may also comprise an electronics assembly 108 operably coupled to the semiconductors 110, 112 and the thermistor 116. The electronics assembly 108 may comprise a controller, processor, or the like operable to control the thermoelectric assembly 102, the cooling system 104, and the like.

The cooling system 104 may comprise one or more microfluidic channels 120, 122. A first microfluidic channel 120 may be fluidly connected with a first conduit (not shown) at the first end 1106 of the device 100, and a second microfluidic channel may be fluidly connected with a second conduit (not shown) at the first end 1106 of the device 100. In some aspects, the first microfluidic channel 120 may be arranged to direct a supply of fluid from the first end 1106 of the substrate 106 to the second end 1206. The second microfluidic channel 122 may be arranged to direct fluid from the second end 1206 of the substrate 106 to the first end 1106. The first and second channels 120, 122 may be fluidly connected proximal the second end 1206 of the substrate 106. According to various aspects, the first channel 120 may direct a cooling fluid from the first conduit to the second end 1206 of the substrate, and the second channel 122 may direct the cooling fluid back to the second conduit at the first end 1106 of the substrate 106. It should be appreciated that the roles of the first and second channels 120, 122 may be reversed in some embodiments.

The device 100 may include a third microfluidic channel 124 fluidly connected with a third conduit (not shown) and arranged to direct a supply of fluid from the first end 1106 of the substrate 106 to an outlet 126 disposed between the first and second ends 1106, 1206. According to various aspects, the third channel 124 may direct a therapeutic drug from the third conduit to the outlet 126 for delivery to a desired body tissue. The electronics assembly 108 may be operable to control drug delivery.

The device 100 may also comprise one or more electrodes 128 comprising, for example, iridium, gold, or the like. The electrodes 128 may be configured to deliver electrical stimulation to desired body tissue. The electronics assembly 108 may be operable to control stimulation of body tissue via the electrodes 128.

As shown in FIG. 2, according to various aspects, the thermoelectric assembly 102 may be associated with a relatively thin dielectric membrane 240 extending from a first portion 242 of the substrate 106 to a second portion 244 of the substrate across a gap 246 between the first and second portions 242, 244. The dielectric membrane 240 may comprise, for example, any known dielectric. The device may also include one or more dielectric layers 250, 252 arranged to passivate the device 100. The dielectric layers 250, 252 may comprise any known dielectric.

In operation, the semiconductor-metal junction may be used to absorb or release heat depending on the direction of the current flowing there through. Because of the difference in Peltier coefficient of the n-type and p-type semiconductors 110, 112 and depending on the direction of the current, this junction will either release or absorb heat at a rate proportional to the magnitude of the current flow. According to various aspects, silicon germanium (SiGe) may be chosen as the construction material for the thermoelectric device because of its relatively high thermal transport efficiency and process compatibility. For example, SiGe has a Peltier coefficient about one order of magnitude larger than many metals and a thermal conductivity five times smaller than polysilicon. SiGe may therefore provide better efficiency in transporting heat than polysilicon.

The arrangement of the thermoelectric assembly 102, the dielectric membrane 240, and the gap 246 may help to confine the heating/cooling process to the thermoelectric assembly 102 and minimize undesired heat conduction to the substrate 106. The gap 246 may be formed, for example, by blocking boron diffusion on the intended gap area, followed by a wet etching in ethylene diamine pyrochatechol (EDP) or potassium hydroxide (KOH), which may etch away lightly doped silicon but not highly-boron-doped silicon. Since dielectrics such as, for example, silicon dioxide and silicon nitride, are poor thermal conductors, heat conduction to the substrate may be reduced by as much as about 95%. The gap 246 may be filled with a gel or polymer having poor thermal conductivity towards the end of the microfabrication process of the device 100 or substrate 106.

In order to remove the heat evolved by the thermoelectric assembly 102 at the second end 1206 of the substrate 106, the microfluidic channels 120, 122 may be monolithically integrated on the substrate 106 via bulk-micromachining and configured to introduce cooling fluid, for example, water. The microfluidic channels 120, 122 may be formed on the substrate 106 using, for example, a selective wet etching and a sealing process with, for example, thermal oxide and low-pressure chemical vapor deposition (LPCVD) deposited dielectrics.

The fluids characteristics in this kind of microchannel were studied experimentally and the flow-rate pressure relationship has been characterized. For a thermoelectric device, for a one-dimensional case, the net heat flux at a heterojunction is:

$$\frac{dQ}{dt} = (\alpha_a - \alpha_b) T x I - k A \frac{dT}{dx}$$

where dQ/dx is the heat energy transported in or out of the junction, $\alpha_a$ and $\alpha_b$ are the Seebeck coefficients of materials forming the heterojunction, T is the absolute temperature at the junction (in ° K.), I is the current flowing through the junction, k is the thermal conductivity of the material, and A is the junction area.

As an estimate of the power required to produce a local temperature rise or drop in tissue or cells, a heat transfer model was used to calculate the temperature variations in tissue as the thermoelectric assembly 102 is turned on. Since more than about 90% of body tissue is water, the heat conductivity and capacity of water were used in this calculation to approximate that of tissue. In addition to heat conduction, heat transfer due to blood flow plays a role in the heating/freezing process of the device 100. According to previous experimental data in thermal marking of brain tissue using conventional micro-heater probes, blood flow cooling accounts for up to ¼ of the power involved in a cell-scale heating process. An estimate was therefore made based on these data. Heat convection may be calculated by Newton's law of cooling:

$$Q = hA(T_W - T_\infty)$$

where Q is the heat flow due to convection (watt), h is the heat-transfer coefficient, A is the surface area of the thermoelectric device, $T_W$ is the temperature of the thermoelectric device, and $T_\infty$ is the temperature of the main body of the cooling fluid.

The contributions of these three main heat transfer mechanisms may be added together to estimate the heating/cooling of tissue/cells using the device 100. It has been found that a heat flux in the order of milli-watt is enough to cool or heat desired tissue for tens of degrees Celsius on a 30 μm-diameter area. For example, a heat flux of 13 milli-watts is able to freeze cell-size tissue. If SiGe is used as the thermoelectric material of the n-type and p-type semiconductors 110, 112, thermally parallel connection of several (p)SiGe-metal-(n) SiGe pairs may be able to transport the required heat flux using a current flow of the order of sub-milli-ampere across each junction. In order to monitor the cell temperature on situ, the semiconductor thermistor 116 may be integrated in the vicinity of the thermoelectric assembly 102. A temperature resolution of 0.3° C. or better resolution may be achieved if appropriate doping is applied on the polysilicon or SiGe film of the semiconductors 110, 112.

Figure 3A:
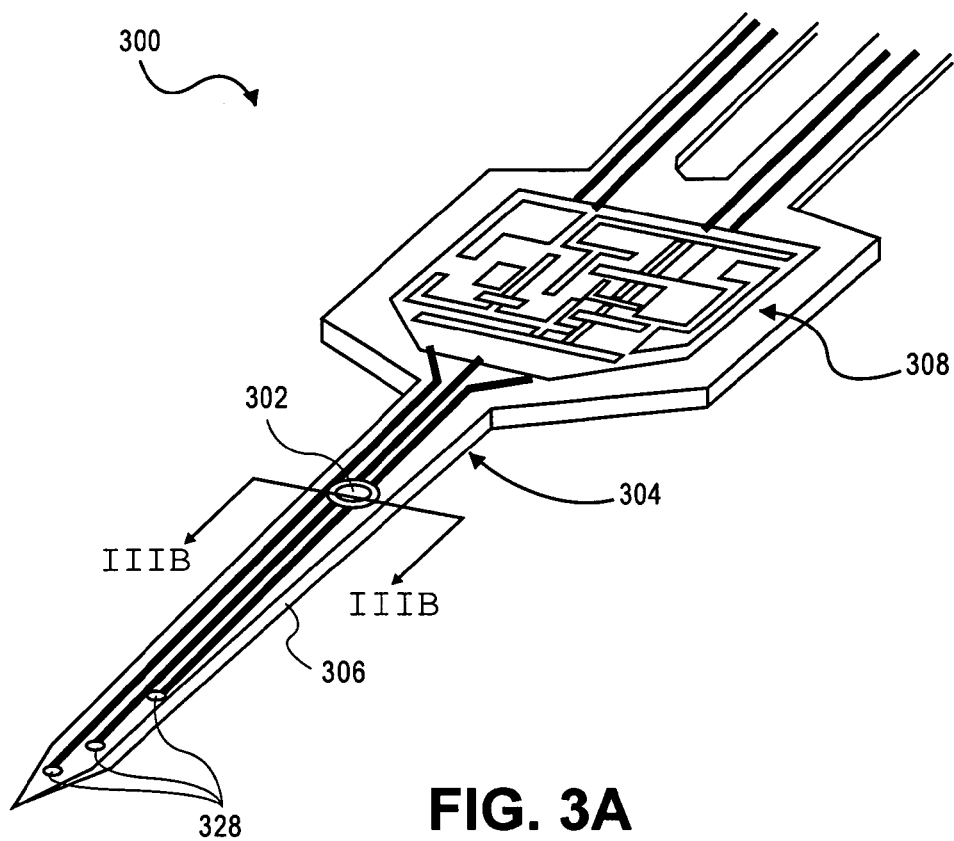
FIG. 3 is a cross-sectional view of an exemplary microfluidic channel in accordance with various aspects of the disclosure.
Figure 3B:
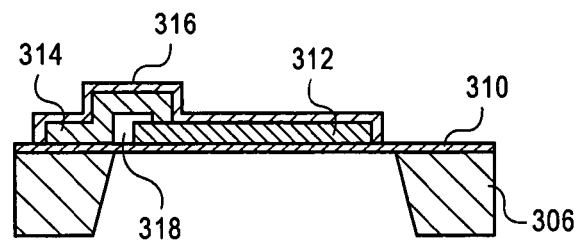

Referring now to FIGS. 3A and 3B, an exemplary medical device 300 may comprise a probe 304 including a thermoelectric assembly 302 associated with a substrate 306, for example, a single crystalline silicon substrate. The thermoelectric assembly 302 may comprise, for example, a microheater and a temperature sensor. The device 300 may also comprise an electronics assembly 308 comprising, for example, a controller, a processor, or the like, configured to operably control the thermoelectric assembly. In combination with the sensor, closed loop control of the heating of the device 300 may be achieved. According to various aspects, the device 300 may include a ribbon cable 320 configured to electrically connect the electronics assembly 308 with external electronics (not shown).

The device 100 may also comprise one or more electrodes 328 comprising, for example, iridium, gold, or the like. The electrodes 328 may be configured to deliver electrical stimulation to desired body tissue. The electronics assembly 308 may be operable to control stimulation of body tissue via the electrodes 328.

As shown in the cross-sectional view of FIG. 3B, the thermoelectric assembly 302 may comprise a dielectric layer 310 on the substrate 306, and a polysilicon layer 312 on the dielectric layer 310. The polysilicon layer 312 may be in contact with a silicide 314, which is also on the dielectric layer 310, and may be spaced from the silicide 314 by a gap 318. The polysilicon layer 312 and the silicide 314 may be covered with another dielectric layer 316.

Figure 4A:
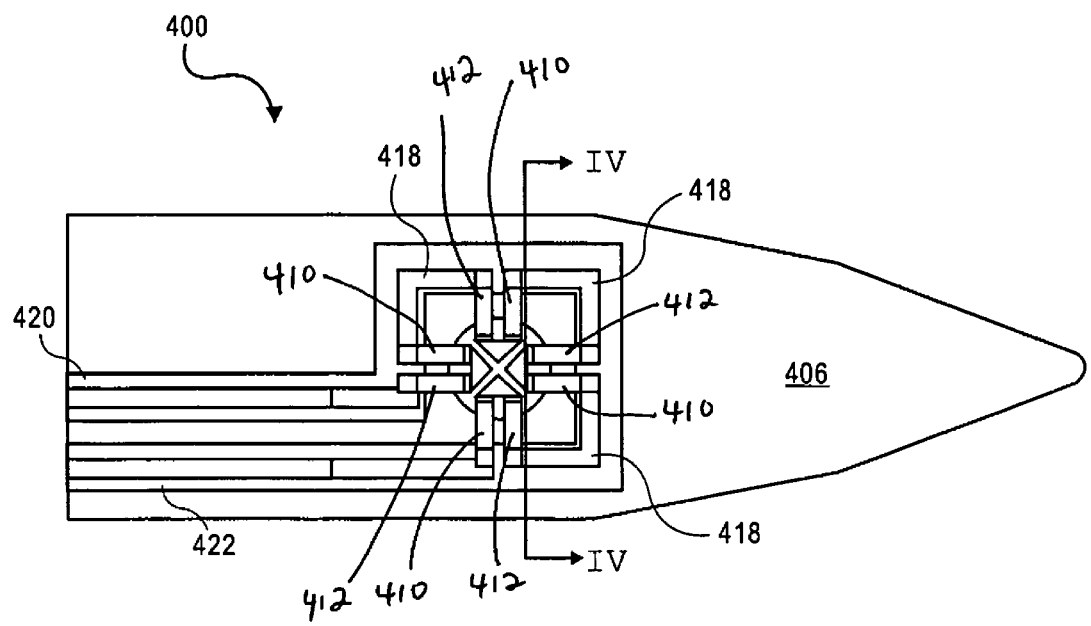
FIG. 4 is a perspective view of an exemplary medical device in accordance with various aspects of the disclosure.
Figure 4B:
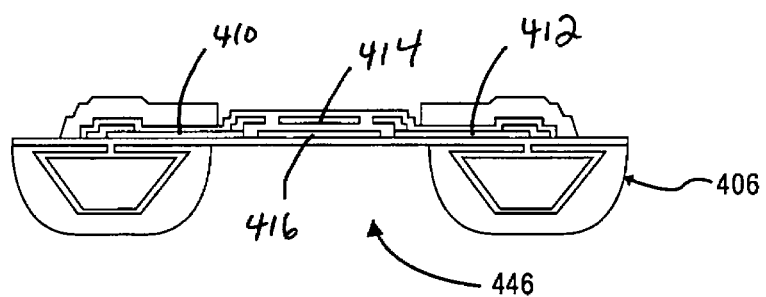

Referring now to FIGS. 4A and 4B, an exemplary medical device 400 may comprise a thermoelectric assembly 402 associated with a substrate 406, for example, a micro-machined silicon substrate. As shown in the cross-sectional view of FIG. 4B, microfluidic channels 420, 422 may be used to introduce fluid, for example, water, for cooling the thermoelectric assembly 402 and to carry the fluid away from the assembly 402. As illustrated in FIG. 4, the thermoelectric assembly 402 may comprise four pairs of n-type and p-type semiconductors 410, 412. Each n-type semiconductor 410 may be electrically connected to a p-type semiconductor via a metal interconnect 414. In addition, the pairs of semiconductors 410, 412 may be electrically connected to one another via metal interconnects 418. It should be appreciated that an n-type semiconductor of one pair and a p-type semiconductor of another pair are connected to the electronic assembly (not shown). According to various exemplary aspects, the thermoelectric assembly 402 may be integrated on a dielectric membrane 440 suspended across a gap 446 in the substrate 406. This design may minimize the heat conduction from the thermoelectric assembly 402 to the substrate 406. The pairs of interconnected semiconductors 410, 412 may be connected in parallel thermally but in series electrically.

The aforementioned exemplary medical devices 100, 300, 400 may produce accurate and predictable temperature disturbance in a small, localized region of tissue. For example, the medical devices 100, 300, 400 may be capable of freezing a small area of tissue or a single cell to enable the study of cell behavior at low temperatures, for clinical application of inhibiting cell activities, in cryoablation, as well as in many other medical treatments. The exemplary devices 100, 300, 400 may also enable cell-scale tissue freezing in vivo. At low temperatures, cell activities slow down and many interesting biological phenomena become prominent. Due to lower metabolism, some special cellular level surgical operation is possible only at low temperatures. The exemplary medical devices 100, 300, 400 may enable the study of cell biology at low temperatures, which may lead to new approaches for tumor/cancer treatment. In various aspects, the application of localized heating may have practical applications both in hyperthermia and histology. Further, in some aspects of the medical devices 100, 300, 400, drug delivery channels, including multi-point drug delivery networks may provide chemical treatment of body tissue.

Using liquid nitrogen (or other low-temperature liquids) flowing through a 23 millimeter pipe to freeze cells/tissue has poor control on the freezing area. Conventional cryosurgery therefore could damage the adjacent health tissue and ducts/blood vessel, causing side effect in this kind of treatment process. In addition, conventional cryosurgery cannot accurately control the freezing rate (temperature change with time). Freezing rate play an important factor in determining the effectiveness of cell killing in a cancer treatment process.

This exemplary devices 100, 300, 400 disclosed herein are capable of freezing/heating tissue with a resolution at the cellular level. In other words, the devices 100, 300, 400 can freeze or heat a single cell. In addition, by controlling the magnitude of the driving current flowing through the thermoelectric assembly 102, 302, 402, the freezing/heating rate can be accurately controlled.

For example, according to various exemplary aspects, the medical devices 100, 400 may comprise a hair-sized silicon probe that can be implanted/inserted in delicate organs (e.g., brain, liver, or the like) with minimal disruption to the organs. The high-resolution freezing and heating capability of the devices 100, 400 may minimize the side effect of cryosurgery by, for example, minimizing damage to healthy tissue and/or blood vessel, ducts or the like.

It should be appreciated that, similar to medical device 100, medical device 400 may include one or more additional microfluidic channels (not shown in FIG. 4) arranged to direct a supply of fluid, for example, a therapeutic drug, to one or more outlets (not shown) in the substrate 406. For example, the additional microfluidic channels may be integrated on the substrate 406. The exemplary device 400 may therefore be able to deliver drugs in precise quantities to cells. In combination with the ability to freeze and/or heat body tissues, the ability to deliver drugs allows the device 400 to be used for multi-step treatment.

Figure 5:
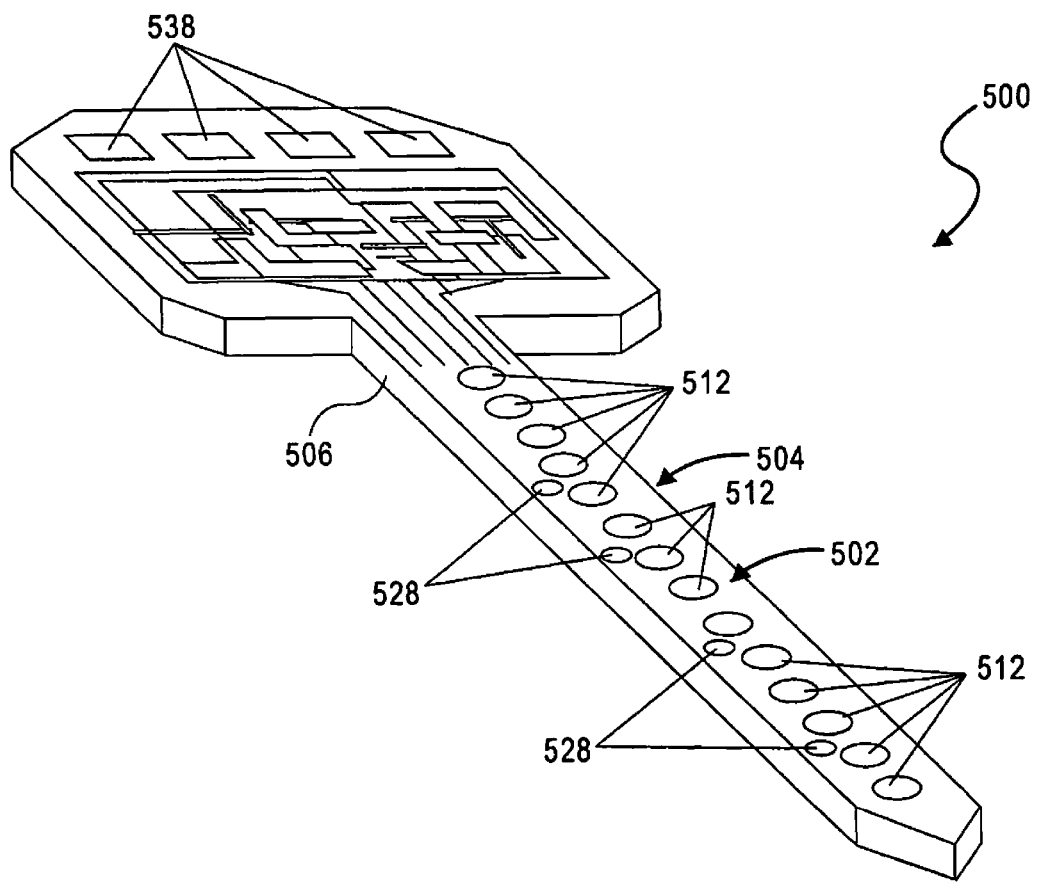
FIG. 5 is a cross-sectional view along line V-V of FIG. 4.

Referring now to FIG. 5, an exemplary medical device 500 may comprise a probe 504 including a transducer array 502 associated with a substrate 506, for example, a micro-machined silicon substrate. The transducer array 502 may be configured for ultrasonic imaging, for example. The array 502 includes a plurality of transducers 512, for example, micro-electro-mechanical-system (MEMS) ultrasonic transducers, examples of which are described in detail below.

The device 100 may also comprise one or more electrodes 528 comprising, for example, iridium, gold, or the like. The electrodes 528 may be configured to deliver electrical stimulation to desired body tissue. The device 500 may also comprise an electronics assembly 508 comprising, for example, a controller, a processor, or the like, configured to operably control the transducer array 502 for ultrasonic imaging and/or control stimulation of body tissue via the electrodes 528. The device 100 may also include bonding pads 538 configured to electrically couple the electronics assembly 308 to external electronics (not shown).

Figure 6:
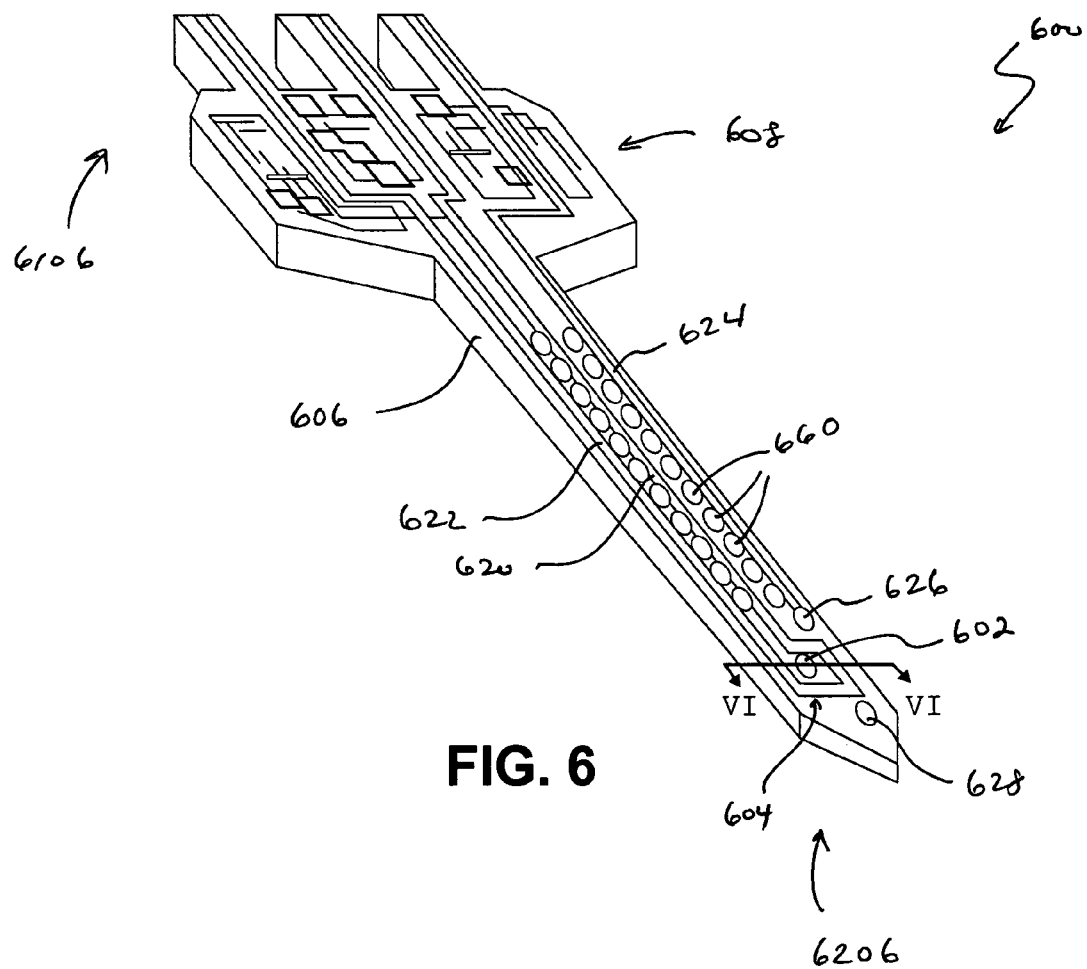
FIG. 6 is a perspective view of an exemplary medical device in accordance with various aspects of the disclosure.

FIG. 6 illustrates an exemplary medical device 600 in accordance with various aspects of the invention. The medical device 600 may comprise a thermoelectric assembly 602 and a cooling system 604 associated with a substrate 606, for example, a micro-machined substrate. The substrate 606 may comprise, for example, silicon, silicon germanium, or any other know substrate. The substrate may have a first end 6106 sized and configured for connection to at least one fluid conduit, for example, a pipette, and a second end 6206 sized and configured for insertion into a body tissue, for example, a human body tissue such as, for example, arteries, organs, or the like, including delicate organs such as the brain and the liver. The second end 6206 may be at an opposite end of the substrate 606 relative to the first end 6106.

The device 600 may also comprise an electronics assembly 608 comprising, for example, a controller, processor, or the like operable to control the thermoelectric assembly 102, the cooling system 104, and the like.

The cooling system 604 may comprise one or more microfluidic channels 620, 622. A first microfluidic channel 620 may be fluidly connected with a first conduit (not shown) at the first end 6106 of the device 100, and a second microfluidic channel may be fluidly connected with a second conduit (not shown) at the first end 6106 of the device 600. In some aspects, the first microfluidic channel 620 may be arranged to direct a supply of fluid from the first end 6106 of the substrate 606 to the second end 6206. The second microfluidic channel 622 may be arranged to direct fluid from the second end 6206 of the substrate 106 to the first end 6106. The first and second channels 620, 622 may be fluidly connected proximal the second end 6206 of the substrate 606. According to various aspects, the first channel 620 may direct a cooling fluid from the first conduit to the second end 6206 of the substrate, and the second channel 622 may direct the cooling fluid back to the second conduit at the first end 6106 of the substrate 606. It should be appreciated that the roles of the first and second channels 620, 622 may be reversed in some embodiments.

The device 600 may include a third microfluidic channel 624 fluidly connected with a third conduit (not shown) and arranged to direct a supply of fluid from the first end 6106 of the substrate 606 to an outlet 626 disposed between the first and second ends 6106, 6206. According to various aspects, the third channel 624 may direct a therapeutic drug from the third conduit to the outlet 626 for delivery to a desired body tissue. The electronics assembly 608 may be operable to control drug delivery.

The device 600 may also comprise one or more electrodes 628 comprising, for example, iridium, gold, or the like. The electrodes 628 may be configured to deliver electrical stimulation to desired body tissue. The electronics assembly 608 may be operable to control stimulation of body tissue via the electrodes 628.

The device 600 may also comprise one or more transducers 660, for example, micro-electro-mechanical-system (MEMS) transducers, which may be configured, for example, as an ultrasound imaging device array for monitoring the anatomical structures of tissue during a cryosurgery or any other medical procedure including procedures involving tissue or cell-level heating and/or freezing.

With this arrangement, the three operations required for a cryosurgery (freezing, heating, and monitoring (temperature sensing and ultrasound imaging)) may be integrated on a micro-sized medical device.

Referring now to FIG. 7A, another exemplary embodiment of the present invention will be described. FIG. 7A is a perspective view of a medical device 700, for example, a micro-sized ultrasound emitter array, in accordance with aspects of the invention. Medical device 700 may comprise, for example, a ribbon cable 702 extending between a first end 704 and a second end 706. The first end 704 may comprise, for example, a portion 708 having one or more bonding pads 710 configured to provide an electrical connection to external electronics (not shown). The second end 706 may comprise a probe 712 including on-chip electronics 714 and a transducer array 716, for example, a MEMS ultrasonic transducer array.

According to various aspects, the probe 712 may comprise, for example, a silicon substrate micromachined, for example, into a probe shape with a cross-sectional dimension, for example, as small as about 40 µm (thickness)×80 µm (width), such that the probe 712 can be implanted into tissue with a minimal disruption. The ribbon cable 702 may comprise a silicon ribbon cable monolithically integrated with the probe 712 to provide electrical connection between the transducer array 716 and the external electronics (not shown). The monolithic silicon ribbon cable may replace a bulky catheter typically used on conventional intravascular ultrasound devices.

Referring now to FIG. 7B, the ribbon cable 702 may comprise a substrate 720, for example, a silicon substrate. According to some aspects, the substrate 720 may comprise a single crystal silicon substrate having a thickness of about 3 µm. The substrate 720 may be coated with a dielectric layer 722 comprising any known dielectric and a semiconductor layer 724 comprising, for example, doped polysilicon or silicide. The semiconductor layer 724 may fabricated, for example, via etching or any other known process, to form one or more counter electrodes as shown in FIG. 7B. A second dielectric layer 726 may coat the semiconductor layer 724 and fill between the counter electrodes. A passivation layer 728 comprising, for example, PECVS oxide and/or parylene C film, may be coated on the second dielectric layer 726.

Turning to FIG. 7C, the probe 712 may comprise a substrate 730 comprising, for example, a micro-machined silicon substrate. According to various aspects, the substrate 730 may have a thickness of about 20 µm to about 70 µm. The transducer array 716 may comprise transducers 718, for example, thin-film drum-structured ultrasonic transducers, integrated on the substrate 730. As shown in the cross-sectional view of FIG. 7C across a pair of transducers, the substrate 730 may be coated with a dielectric layer 732 comprising, for example, any known dielectric, and a semiconductor layer 734 comprising, for example, doped polysilicon or polycide. The semiconductor layer 734 may fabricated, for example, via etching or any other known process, to form one or more counter electrodes 736 as shown in FIG. 7C. A membrane 738, for example, a doped polysilicon or polycide membrane, may be suspended above the counter electrodes 736 on the substrate 730 and separated from the counter electrode 736 by a gap 742. The membrane 738 may be insulated from the counter electrodes 736 by the dielectric layer 732. One or more passivation layers 740 comprising, for example, PECVS oxide and/or parylene C film, may be coated on the membrane 738.

In operation, the drum-structured transducers 718 may emit and sense ultrasounds. For example, upon application of an ac electrical signal between the membrane 738 and the counter electrode 736, the electrostatic force will drive the membrane 738 to vibrate and send out acoustic waves. The space between the suspended membrane 738 and the counter electrode 736 may be vacuum-sealed such that tissue fluids will not flow into this region during operation. In order to minimize parasitic capacitance and reduce RC delay, the width of metal electrical interconnects (not shown) are reduced to the minimum achievable with the fabrication process.

In designing device 700, five specification parameters may be used to determine the performance of the transducer array 716. These parameters include the resonant frequency of the suspended membrane 738, the maximum vertical displacement (which may chosen based on the desired application of the device 700) of the membrane 738, the pull down voltage, the bias voltage, and the maximum pressure delivered by the vibration of the membrane 738. According to various aspects, the membrane 738 may be, for example, circular, hexagonal, or other desired shape. According to some aspects, a hexagonal transducer may be used to achieve a better area efficiency for the two dimensional arrays. For a simple circular membrane with a clamped boundary, the resonant frequency can be determined by the following analytical equation:

$$\omega_{ns} = \frac{\lambda_{ns}}{R^2}\sqrt{\frac{K}{\mu}}$$

where R is the radius of the membrane of uniform thickness, $\lambda_{ns}$ is a numerical value for circular membrane, $\mu=\rho t$ is the mass of the plate per unit area ($\rho$ is the plate material density, t is the plate thickness), and $K=Et3/12(1-v2)$ is the bending stiffness (E is the Young's modulus of the membrane material, v is the Poisson's ratio). However, as this device may be operated in tissue fluids, the influence of damping should be included, and a numerical method may be used to find out the resonant frequency. The center deflection of a clamped circular plate under a uniform pressure can be found from the following equation:

$$P = \frac{Eh^4}{R^4}\left[\frac{16y}{3(1-v^2)h} + \frac{(7-v)y^3}{3(1-v^2)h^3} + \frac{4R^2\sigma y}{(1-v)Eh^3}\right]$$

where P is the uniform pressure applied on the membrane, y is the center deflection, and $\sigma$ is the intrinsic stress of the membrane material. This equation can be used to estimate the pressure of the ultrasound waves under a prescribed membrane deflection. In the exemplary device 700, the vertical membrane displacement required for the ultrasonic diagnosis or imaging may be in the order of several hundred angstroms.

To minimize the driving voltage and improve the sensitivity of the transducer array 716, the gap height between the membrane 738 and the counter electrode 736 may be made as small as possible. The membrane thickness and diameter may then determined by the surface pressure requirement and the resonant frequency. With all these parameters decided, the pull down voltage and the bias voltage can be determined.

To avoid direct exposure of the tissue/cells to high electrical fields, the suspended membrane 738 may be connected to an electrical ground (not shown) while the counter electrode 736 may be connected to an electrical signal line (not shown). As the membrane 738 may be made of highly conductive material, the shielding effect may constrain the electric filed in the region under the membrane 738. In order to insulate the membrane 738 from the tissue fluids and to protect it from tissue fluids corrosion, the layers of PECVS oxide and parylene C film 740 may be coated on the surface of the membrane 738 as the passivation layers. The passivation parylene C film may also improve the device bio-compatibility.

According to various exemplary aspects, the length of the probe 712 may range from about 1 to about 10 millimeters, depending on how many ultrasound transducers 718 are to be integrated on the transducer array 716. It should be appreciated that any one- or two-dimensional array can be integrated on the probe substrate 730. It should be appreciated that a two-dimensional array can also be assembled to form a three-dimensional ultrasonic array. It should be appreciated that by integrating an array of membranes 738 of different geometrical dimension, a broad frequency spectrum can be generated and sensed from the transducers 718 on the same substrate 730 built by the same fabrication process.

In order to avoid potential process compatibility and stress problems associated with boron doping in a conventional dissolving wafer process, a double-sided dry etching micromachining process can be used on a regular silicon wafer to form micro probes as the substrate for the medical device 700. Different from conventional silicon-on-insulator (SOI) micro-machined probes, the probe 712 comprises a regular silicon wafer as the substrate, which may provide a cost advantage. Similar to SOI silicon probes, the present device 700 is able to achieve an accuracy in the substrate dimension control to within ±1 μm.

Figure 8A:
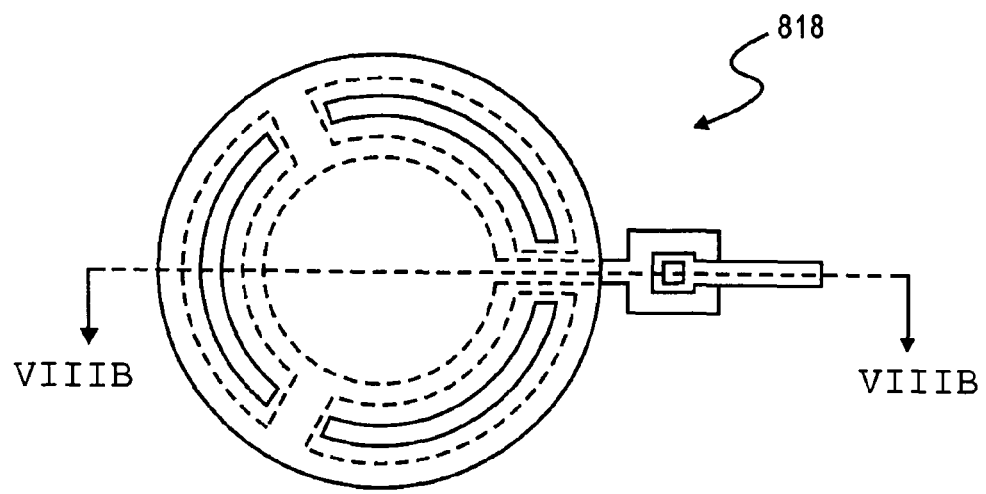
FIG. 8 is a perspective view of an exemplary medical device in accordance with various aspects of the disclosure.
Figure 8B:
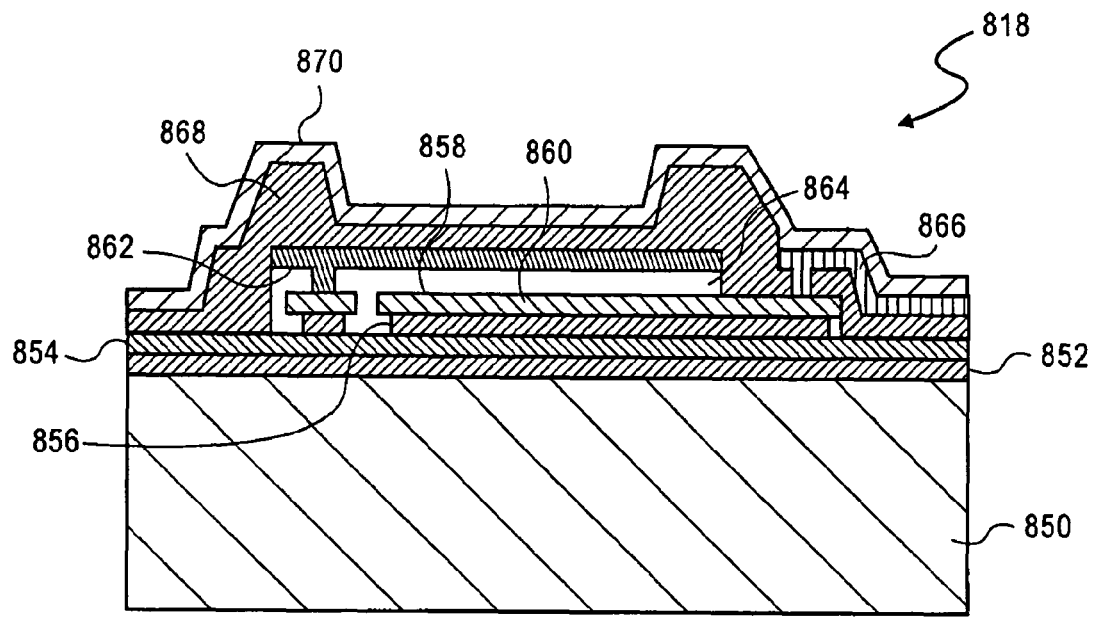

Referring now to FIGS. 8A and 8B, another exemplary transducer 818 is described. The transducer 818 may be used in place of the transducer 718, for example, in the medical device 700 described above. The transducer 818 may comprise a substrate 850 such as, for example, a silicon substrate having a doped surface. The transducer 818 may also comprise a dielectric layer of, for example, thermal oxide 852 such as, for example, silicon dioxide, grown on the substrate surface. Two additional dielectric layers 854, 856 may overlie the layer of thermal oxide. The second dielectric layer 854 may comprise, for example, silicon nitride, and the third dielectric layer 856 may comprise, for example, silicon dioxide.

A semiconductor layer 858, for example, a polysilicon layer or other conducting thin film, is on top of the sandwiched dielectric layers 854, 856. The semiconductor layer 858 may be fabricated by, for example, etching, to form a counter electrode 860. A semiconductor membrane 862, for example, polysilicon, is suspended above the semiconductor layer 856, thereby defining a cavity 864 that may be vacuum-sealed. The transducer 818 may include a metal interconnect 866 such as, for example, aluminum configured to electrically connect the counter electrode 860 with other counter electrodes and/or on-chip electronics.

The transducer 818 may include a layer of deposited oxide 868, for example, silicon dioxide, for sealing the membrane 862, as well as a layer 870 of passivation dielectrics. The layer 870 of passivation dielectrics may include a layer of deposited oxide and/or a layer of parylene C. The layer of parylene C may be relatively thick, for example, in the order of several microns.

Figure 9A:
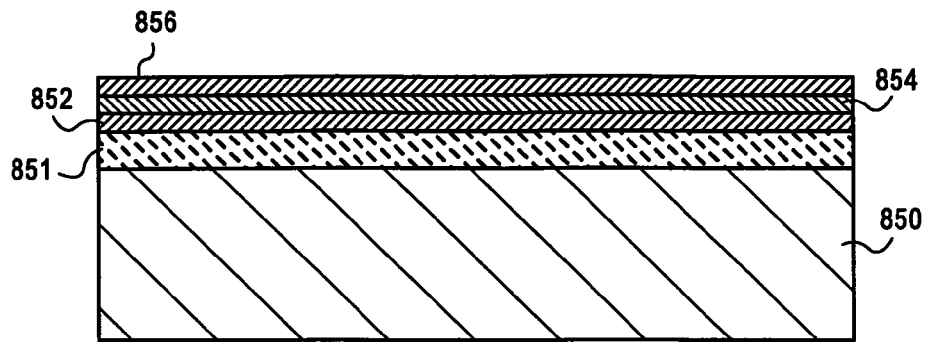
FIGS. 9A-9M are cross-sectional views of an exemplary transducer illustrating an exemplary process in accordance with aspects of the invention.

Referring now to FIGS. 9A-9M, an exemplary process of making the exemplary medical device 800 will be described. As shown in FIG. 9A, the surface of the silicon substrate 850 may be doped using, for example, diffusion or ion implantation to create a highly conducting surface layer 851. This layer 851 may reduce or prevent charge feedthrough to the substrate 850 from the electrostatic devices on the surface.

After the doping process, the layer of thermal oxide 852 may be grown on the surface of the substrate 850 and serve as a first dielectric layer. Two additional dielectric layers, for example, the silicon nitride layer 854 and the silicon dioxide layer 856 may then be deposited on top of the thermal oxide layer 852 using, for example, low pressure chemical vapor deposition (LPCVD) or other known chemical vapor deposition (CVD) processes.

Figure 9B:
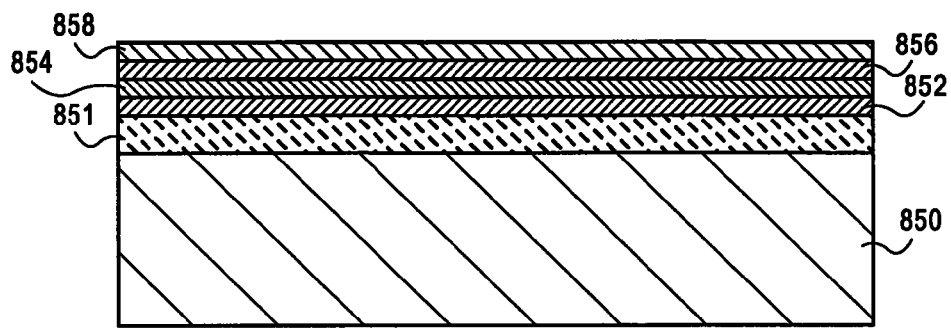

Referring now to FIG. 9B, on top of the sandwiched dielectric layers (e.g., silicon dioxide/silicon nitride/silicon dioxide), the semiconductor layer 858 comprising, for example, polysilicon or other conducting thin film, may be deposited, doped, and annealed to reduce the residual stress. The semiconductor layer 858 may work as a counter electrode for the drum membrane as well as for the electrical interconnects.

Figure 9C:
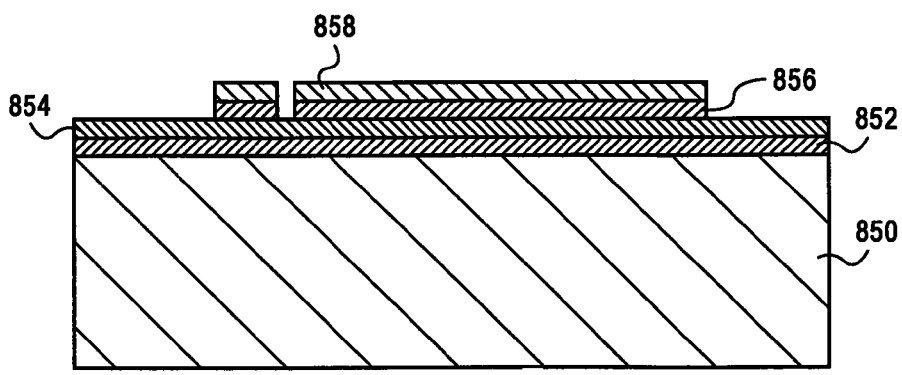

As shown in FIG. 9C, a photolithography process may be used to define patterns of the semiconductor layer 858. A dry etching, for example, hydrogen fluoride (HF) etching, may be used to remove the exposed portion (not covered by a masking photoresist) of the semiconductor layer 858, thus transferring the patterns into the semiconductor layer 858. With the masking photoresist still on, another dry etching, for example, HF etching, may be used to remove the exposed top dielectric layer 856 comprising, for example, silicon dioxide. Thus, the second dielectric layer 854 comprising, for example, silicon nitride, may be exposed everywhere except where the semiconductor layer 858 is still present. The top dielectric layer 856 is thus self-aligned with the semiconductor layer 858 comprising, for example, a polysilicon structure. With this arrangement, the semiconductor layer 858 may be anchored to the substrate 850 through the third dielectric layer 856, which may comprise a silicon dioxide film instead of silicon nitride. However, the remainder of the substrate 850 is covered by the second dielectric layer 854, which may comprise, for example, silicon nitride, that survives from HF etching in the subsequent HF release etching process.

Figure 9D:
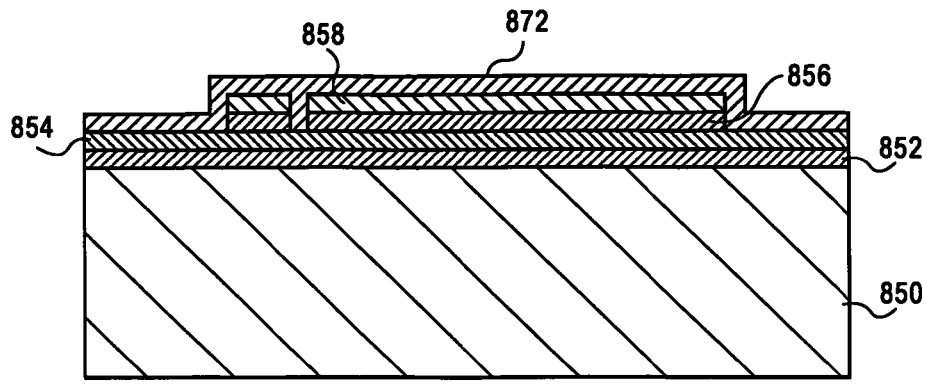
Figure 9E:
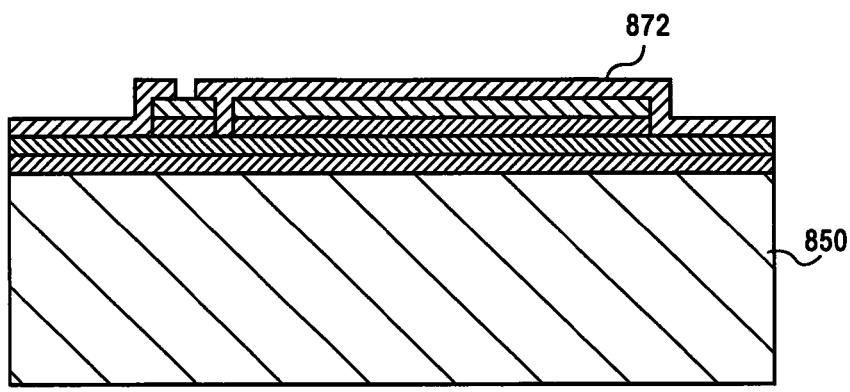

Referring to FIG. 9D, a thin layer of a sacrificial oxide 872 may be deposited next. The thickness of this sacrificial oxide 872 determines the gap height between the membrane and its counter electrode. As shown in FIG. 9E, the sacrificial oxide may be patterned using a photolithography process and a dry etching such as, for example, HF etching, to form dimples (not shown) and anchoring holes.

Figure 9F:
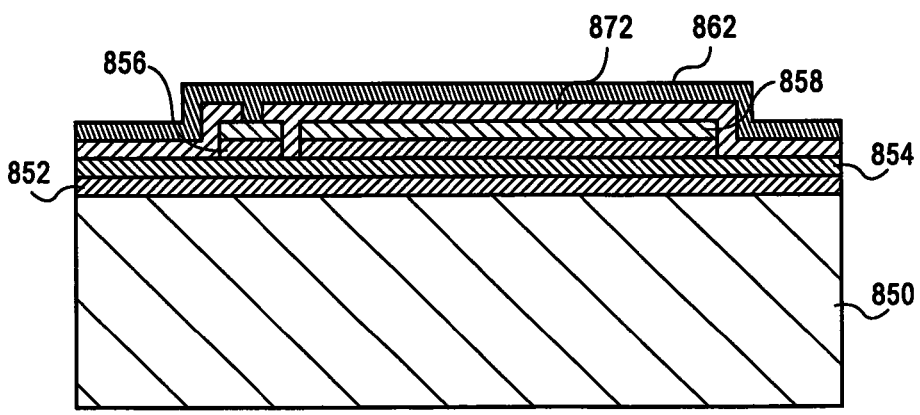
Figure 9G:
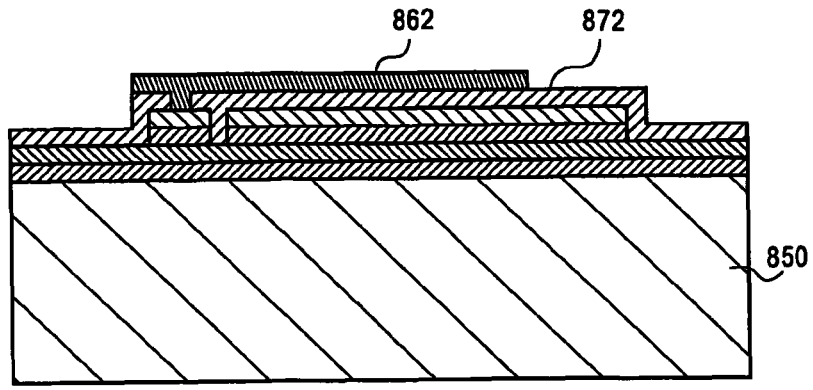

Turning now to FIG. 9F, a second semiconductor layer 862 comprising, for example, structural polysilicon, may be deposited, doped, and annealed. As shown in FIG. 9G, the second semiconductor layer 862 may be patterned to form a membrane using a photolithography process and a dry etching such as, for example, HF etching.

Figure 9H:
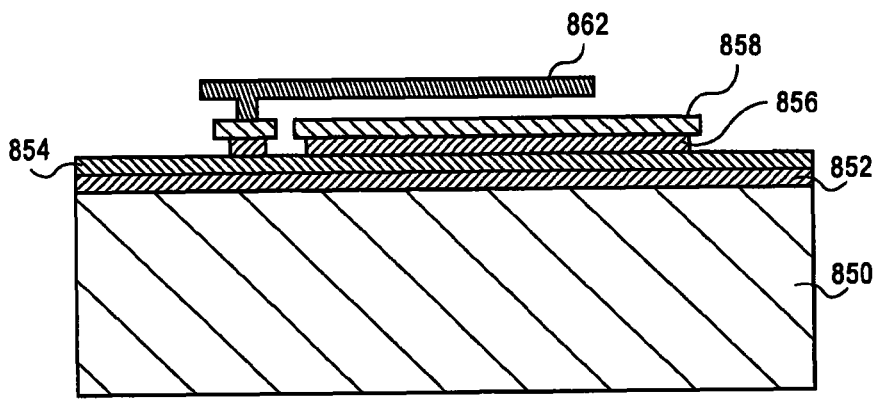

Referring now to FIG. 9H, a conventional dry or wet etching may be used to remove the sacrificial oxide 872 to release microstructures of the second semiconductor layer 862 from the substrate 850. This dry/wet etching may also undercut the thin oxide layer under the first semiconductor layer 858. Due to the etch rate difference between the sacrificial oxide and the high-quality LPCVD oxide under the first semiconductor layer 858, the length of the undercut is small and will not degrade the anchoring robustness of the first semiconductor layer 858.

Figure 9I:
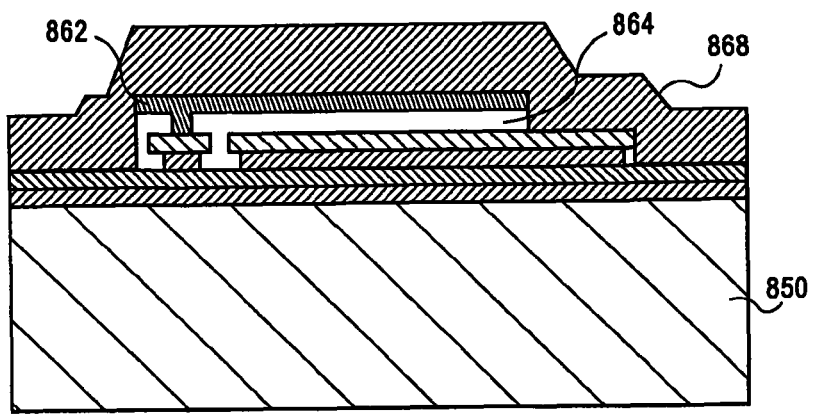
Figure 9J:
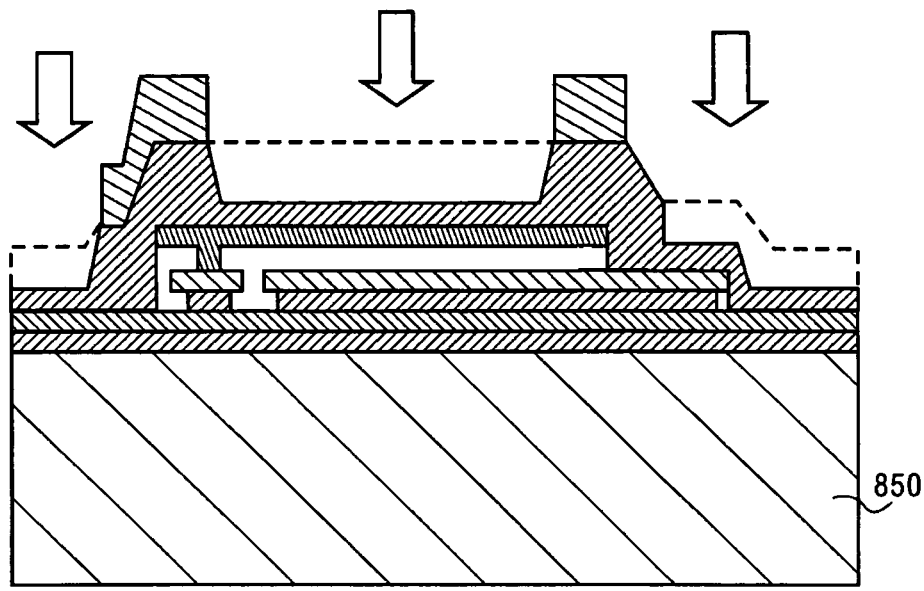

Turning to FIG. 9I, a thick layer of PECVD or other deposited oxide 868 may be used to seal the release holes. As these thin-film deposition processes are performed in vacuum, the cavity 864 under the semiconductor membrane 862 may be sealed under vacuum. A photolithography process and a dry and/or wet etch may be used to pattern the sealing oxide 868 such that the oxide thickness is reduced to about 4000 angstroms on most of the device areas except areas around the release holes and along the edge of the membrane rim, as shown in FIG. 9J.

Figure 9K:
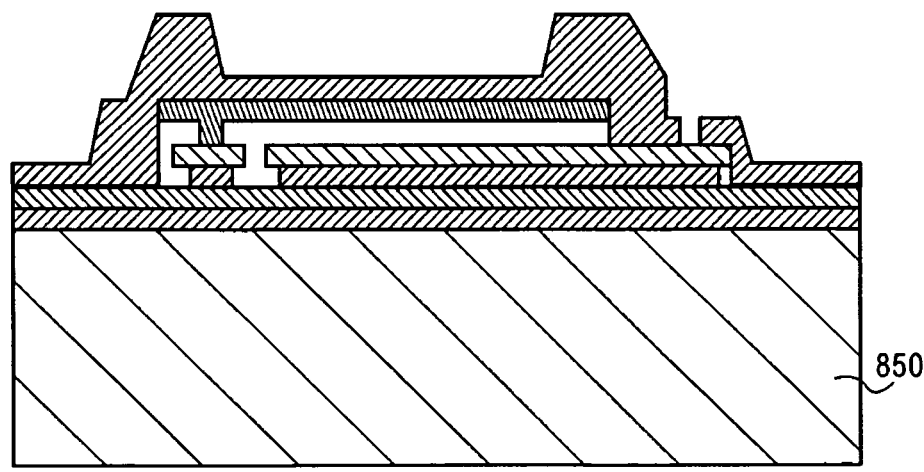
Figure 9L:
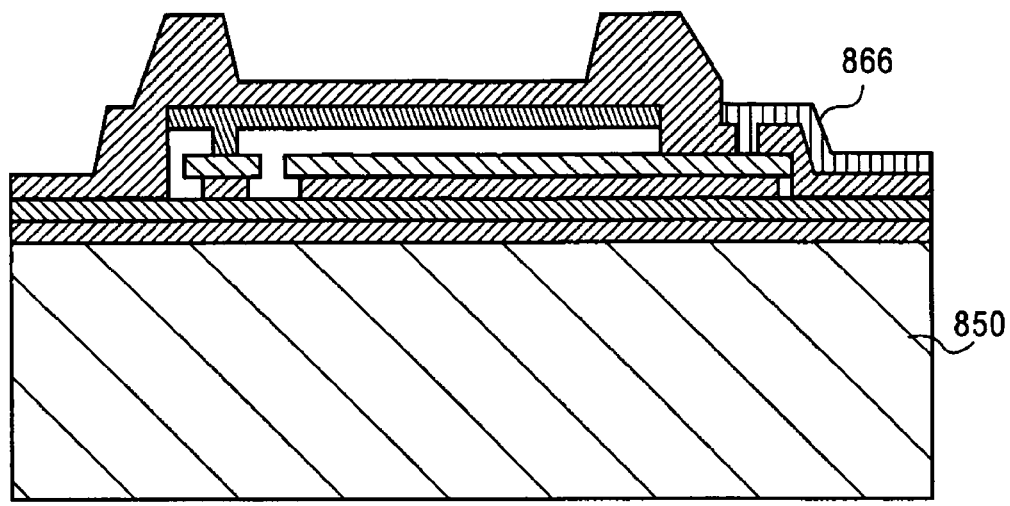
Figure 9M:
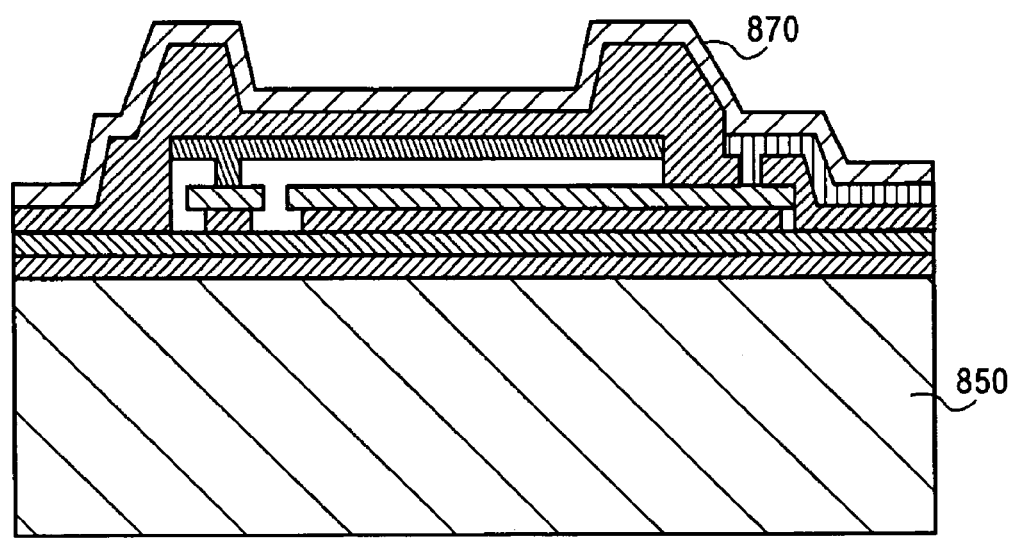

Referring now to FIG. 9K, a photolithography step and a conventional dry and/or wet etching may be used to make openings for receiving a metal layer that may define the metal interconnect 866. The metal layer may be deposited and patterned to form the interconnect 866, as shown in FIG. 9L. Similar to the first semiconductor layer 858, the metal interconnect 866 may anchor to the substrate 850 through the second dielectric layer comprising, for example, silicon dioxide, instead of silicon nitride. This may prevent/minimize charge buildup at the (metal) conductor-nitride interface. This structure (i.e., adding a relatively thick layer of dielectrics under the metal) also reduces the capacitance between the metal interconnect 866 and the substrate 850. Turning to FIG. 9M, the passivation dielectric layer 870 may include a layer of PECVD oxide and/or a relatively thick (e.g., several microns) layer of parylene C.

The exemplary medical device 800 may work both as an emitter to generate ultrasounds and a sensor to detect ultrasounds. When the device 800 works as an emitter, the transducer 818 is driven by an ac electrical signal applied between the membrane 862 and the counter electrode 860. The ac electrical signal may produce a time varying electrostatic force on the membrane 862 that urges the membrane 862 to move up and down. This movement generates mechanical waves which transmit out to the media surrounding the membrane 862. During this electrostatic actuation process, electrical charges are periodically received into and removed from the variable capacitor, which is defined by the membrane 862 and the counter electrode 860.

Figure 10:
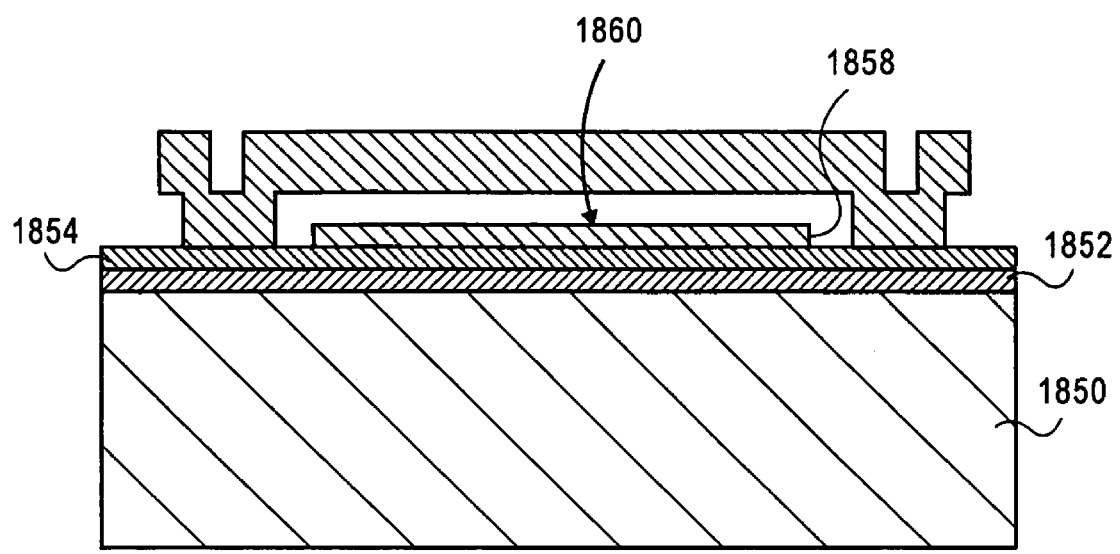
FIG. 10 is a cross-sectional view of a transistor constructed in via conventional fabrication processes.

For drum structures built by conventional polysilicon surface micromachining processes, for example, the U. C. Berkeley polysilicon surface micromachining process or the Sandia Ultra-planar, Multi-level MEMS technology (SUMMiT), the counter electrodes 1860 are generally built by a first polysilicon layer 1858 that lies directly on a silicon nitride layer 1854, which in turn lies on a dielectric layer 1852 and a substrate 1850, as shown in FIG. 10. Silicon nitride has a high density of interface traps which tends to "capture" electrical charges that travel close to them. As a result, more and more charges may be trapped at the silicon nitride-conductor/semiconductor interface after cycles of electrical actuation. Due to buildup of electrical charges at the nitride-conductor interface, higher and higher voltages may be required to actuate the electrostatic devices. This may adversely affect the lifetime and stability of the electrostatic devices built by conventional polysilicon surface micromachining processes. Due to charge buildup, higher and higher voltages may be required to drive the device until this driving voltage is higher than the floor dielectrics can sustain and the device may be subject to breakdown. In addition to happening to moveable microstructures (e.g., a polysilicon comb drive actuator, the capacitive ultrasonic transducer described herein, or other MEMS structures made of silicon nitride film with a conductor film in direct contact with it), charge buildup may also occur on conductor/semiconductor thin film interconnects that are in direct contact with silicon nitride.

In order to prevent/minimize charge buildup, silicon nitride may be prevented from directly contacting the conductor/semiconductor. However, for a polysilicon surface micromachining process for which silicon dioxide is used as the sacrificial layer, a silicon nitride film is needed to insulate the conducting microstructures from the silicon substrate. In order to overcome this dilemma, the exemplary transistor 818 isolates conducting thin films, for example, polysilicon and/or metal, from the silicon nitride film by adding a thin layer of silicon dioxide between them.

Figure 11A:
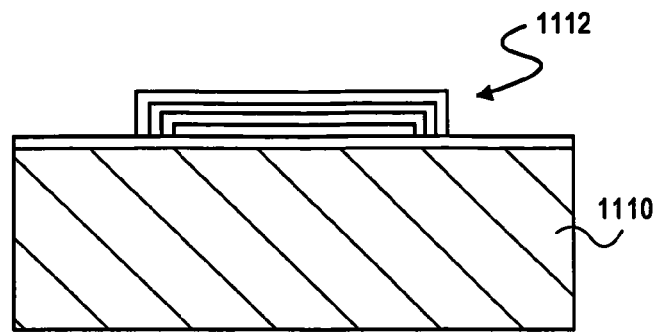
FIGS. 11A-11C show an example process for fabricating a substrate into a probe including an array of ultrasound transducers.
Figure 11B:
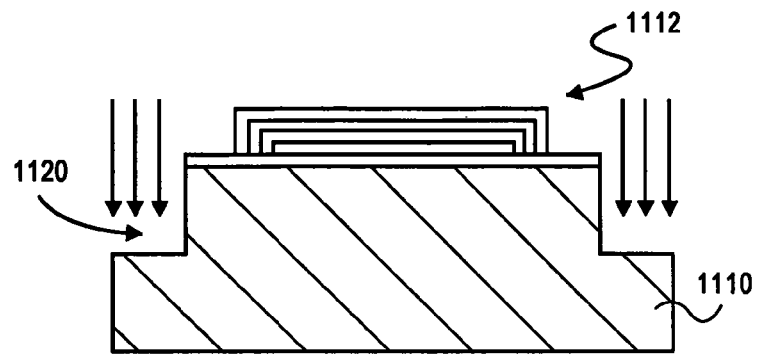
Figure 11C:
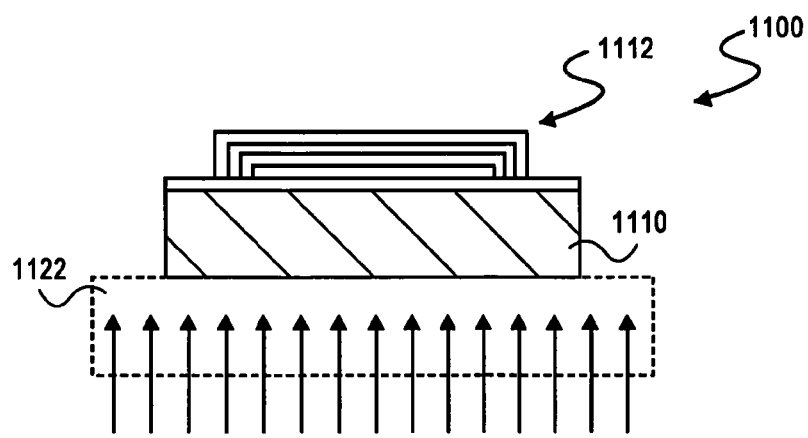

Referring now to FIGS. 11A-11C, an exemplary process for fabricating a substrate into a probe 1100 comprising, for example, an array of ultrasound transducers 1112 is described. The exemplary process may comprise a double-sided dry etching micromachining process on a regular silicon wafer to form micro probes as the substrate for the ultrasound transducer array. Different from silicon-on-insulator (SOI) micromachined probes, a silicon probe fabricated in accordance with the exemplary process of FIG. 11 uses regular silicon wafers as the substrate, which may provide a cost advantage. Similar to SOI silicon probes, the dimensions of a double-side dry etched probe in accordance with the present invention can be controlled to within ±1 μm.

A conventional thin film surface micromachining process can be used to build the ultrasound transducers 1112 and metal electrical interconnects (not shown) on a silicon substrate 1110 (FIG. 11A). After fabrication of the transducers 1112 and interconnect, the substrate 1110 may be fabricated using a double-sided dry etching process. For example, a first side 1120 of the substrate 1110 is fabricated, for example, by a masked dry etching process, as shown in FIG. 11B. As shown in FIG. 11C, the second side 1122 of the substrate 1110 may then be micromachined, for example, using a masked dry etching process.

According to various aspects of the invention, an integrated silicon ribbon cable (not shown) can be formed, for example, via an additional backside photolithography that can create a recess under the silicon ribbon cable area such that after a flood backside etching, the thickness of the ribbon cable is thinner than that of the probe body.

Referring now to FIGS. 12 and 13, an exemplary medical device 1300 may comprise a probe 1304 including at least one transducer 1302, for example, a MEMS capacitive ultrasound transducer, associated with a substrate 1306, for example, a micro-machined silicon substrate. The transducer 1302 may be configured for ultrasonic imaging, for example. The device 1300 may also comprise an electronics assembly 1308 comprising, for example, a controller, a processor, or the like, configured to operably control the transducer 1302 for ultrasonic imaging. It should be understood that the electronics assembly 1308 may be electrically coupled to external electronics (not shown).

As shown in the cross-sectional view of FIG. 13, the transducer 1302 may comprise a dielectric layer 1310 on the substrate 1306, and a counter electrode 1312, for example, a polysilicon electrode or the like, on the dielectric layer 1310. A semiconductor membrane 1314, for example, a polysilicon membrane or the like, may be suspended above the counter electrode 1312 by a gap 1316. The gap 1316 may be defined by a vacuum chamber during the fabrication process. A dielectric layer 1318 may seal the transducer 1302.

The device 1300 may comprise one or more microfluidic channels 1324, 1334, 1344 fluidly connected with supply conduits (not shown) and arranged to direct a supply of fluid from the supply conduit to corresponding outlet(s) 1326, 1336, 1346 disposed between first and second ends 1338, 1340 of the device 1300. According to various aspects, the channel(s) 1324, 1334, 1344 may direct a therapeutic drug to the outlet(s) 1326 for delivery to a desired body tissue. The electronics assembly 1308 may be operable to control drug delivery.

As shown, the ultrasound transducer 1302 may be integrated with one or more of the microfluidic channels 1324, 1334, 1344 to enhance the accuracy, efficiency, and/or directionality of a drug delivery process at the cellular level. For example, as shown in FIGS. 12 and 13, the ultrasound transducer 1302 may be integrated proximal, for example, beside, the drug delivery outlet 1346. The transducer 1302 can emit ultrasounds to generate a "streaming" effect in the drug delivery process, and the pressure waves of the ultrasounds may enhance the directionality and rate of drug delivery via the outlet 1346. The ultrasounds may also increase permeability of the desired cell membrane to promote drug delivery efficiency into the cell.

Although not shown, it should be appreciated that the device 1300 may also comprise one or more electrodes comprising, for example, iridium, gold, or the like. The electrodes may be configured to deliver electrical stimulation to desired body tissue.

Referring now to FIGS. 14 and 15, an exemplary medical device 1500 may comprise a probe 1504 including at least one transducer 1502, for example, a MEMS capacitive ultrasound transducer, associated with a substrate 1506, for example, a micro-machined silicon substrate. The transducer 1502 may be configured for ultrasonic imaging, for example. The device 1500 may also comprise an electronics assembly 1508 comprising, for example, a controller, a processor, or the like, configured to operably control the transducer 1502 for ultrasonic imaging. It should be understood that the electronics assembly 1508 may be electrically coupled to external electronics (not shown).

As shown in the cross-sectional view of FIG. 15, the transducer 1502 may comprise a dielectric layer 1510 on the substrate 1506, and a counter electrode 1512, for example, a polysilicon electrode or the like, on the dielectric layer 1510. A semiconductor membrane 1514, for example, a polysilicon membrane or the like, may be suspended above the counter electrode 1512 by a gap 1516. The gap 1516 may be defined by a vacuum chamber during the fabrication process. A dielectric layer 1518 may seal the transducer 1502.

The device 1500 may comprise one or more microfluidic channels 1524, 1534, 1544 fluidly connected with supply conduits (not shown) and arranged to direct a supply of fluid from the supply conduit to corresponding outlet(s) 1526, 1536, 1546 disposed between first and second ends 1538, 1540 of the device 1500. The flow channels 1524, 1534, 1544 may comprise a polymer, for example, parylene C, SU-8, or the like, using relatively thick photoresistive materials or the like as the sacrificial layer. According to various aspects, the channel(s) 1524, 1534, 1544 may direct a therapeutic drug to the outlet(s) 1526, 1536, 1546 for delivery to a desired body tissue. The electronics assembly 1508 may be operable to control drug delivery.

As shown, the ultrasound transducer 1502 may be integrated with one or more of the microfluidic channels 1524, 1534, 1544 to enhance the accuracy, efficiency, and/or directionality of a drug delivery process at the cellular level. For example, as shown in FIGS. 14 and 15, the ultrasound transducer 1502 may be integrated beneath the drug delivery outlet 1534. The transducer 1502 can emit ultrasounds to generate a "streaming" effect in the drug delivery process, and the pressure waves of the ultrasounds may enhance the directionality and rate of drug delivery via the outlet 1544. The ultrasounds may also increase permeability of the desired cell membrane to promote drug delivery efficiency into the cell.

Due to their miniature size, the exemplary medical devices disclosed herein can reach deep inside the tissue with a minimal disruption. As a result of being proximal a target cell, tissue, and/or organ, various aspects of these devices can generate high-frequency ultrasounds to stimulate tissue and/or cells or detect biological information, for example, cell/tissue temperature, blood flow rate, and the like, from a localized area of tissue without significant disturbance to neighboring healthy tissue.

In some aspects, these devices are smaller than a human hair, and therefore can be implanted in blood vessel for clearing plaque using high-frequency, high-power ultrasounds. These plaque-clearing ultrasounds may be used without drug delivery or in combination with drug delivery. Also, these ultrasounds will not propagate too far beyond the target area to damage the neighboring healthy tissue. In addition, these devices may be used to detect an abnormality of a vessel structure or to measure blood flow rate using the principle of Doppler ultrasounds. Due to penetration depth limit (which is associated with the wavelength of the ultrasound waves), ultrasounds applied from outside of the body are not capable of measuring blood flow rate of fine vessels inside the tissue.

Some aspects of the medical devices disclosed herein may also be used for high-precision tissue heating using ultrasounds. The high-frequency ultrasounds generated from this tool may better focus on a target tissue and minimize unwanted heating to neighboring tissue. For example, these devices may be useful many clinical treatments, including killing of cancer cells, using high heat. In addition to heating, these exemplary devices can be used to measure tissue temperature. The travel speed of ultrasound waves in tissue depends on tissue temperature. By measuring the traveling speed of ultrasounds in tissue, the temperature of tissue can be identified. For long-wavelength ultrasound applied from outside of the body, the ultrasound waves travels a long distance across different kind of tissue and the speed-temperature relation is difficult to uniquely determine. However, by using high-frequency ultrasound waves emitted and detected from a point close to the target tissue, the traveling speed of ultrasounds can accurately indicate the tissue temperature.

As discussed above, the exemplary devices comprising one or more ultrasound transducers integrated with microfluidic channels may delivery therapeutic drugs to a target tissue or cell with enhanced the accuracy, efficiency, and directionality. The ultrasound transducers integrated proximal a drug delivery outlet may emit ultrasounds to generate a "streaming" effect in a drug delivery process. The pressure wave of ultrasounds may enhance the directionality and rate of drug delivery. In addition, the ultrasound may increase a cell membrane's permeability to promote the drug delivery efficiency into the cell.

In other aspects, the exemplary medical devices comprising one or more implantable ultrasound transducers may also be used to accelerate the healing rate of a wound or for stimulating neurons and altering the behavior of neurons.

It will be apparent to those skilled in the art that various modifications and variations can be made to the audio systems and methods of audio communication of the present invention without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A micro-sized, medical probe configured to be inserted into body tissue, the probe comprising:
   a micro-machined substrate;
   at least one thermo-electric assembly having a n-type semiconductor region, a p-type semiconductor region, and a metal interconnect electrically coupling said n-type semiconductor region and said p-type semiconductor region with one another, said at least one thermo-electric assembly monolithically integrated on said micro-machined substrate, said thermo-electric assembly being operable to selectively perform heating and freezing processes with respect to body tissue proximal the probe after insertion of the probe into body tissue, said heating and freezing processes based on operation of said metal interconnect electrically coupling said n-type semiconductor region and said p-type semiconductor region; and
   two microfluidic channels monolithically integrated in said micro-machined substrate, said two microfluidic channels separated by a gap region in said micro-machined substrate with a membrane over said gap region, said membrane extending across said two microfluidic channels with said n-type semiconductor region and said p-type semiconductor region disposed on said membrane, at least one of said two microfluidic channels being configured to direct fluid to and from a region of said micro-machined substrate proximal said thermo-electric assembly so as to confine said heating and freezing processes to said thermo-electric assembly.

2. The medical probe of claim 1, further comprising at least one electrode configured to stimulate a body tissue proximal the probe after insertion of the probe into body tissue.

3. The medical probe of claim 1, further comprising an electronics assembly configured to control at least one of said heating and freezing processes of said thermo-electric assembly and said direction of fluid to and from said region of said micro-machined substrate proximal said thermo-electric assembly via said at least one microfluidic channel.

4. The medical probe of claim 3, further comprising a temperature sensor, said temperature sensor cooperating with said electronics assembly to provide bi-directional temperature control of said thermo-electric assembly.

5. The medical probe of claim 1, wherein said thermo-electric assembly comprises a plurality of semiconductor-metal junctions, each of the semiconductor-metal junctions disposed across a respective pair of microfluidic channels monolithically integrated in said micro-machined substrate.

6. The medical probe of claim 1, further comprising at least one transducer associated with said micro-machined substrate, said transducer being configured to send and receive ultrasonic waves to image body tissue proximal the probe after insertion of the probe into body tissue.

7. A micro-sized, medical probe configured to be inserted into body tissue, the probe comprising:
   a micro-machined substrate;
   at least one thermo-electric assembly having a n-type semiconductor region, a p-type semiconductor region, and a metal interconnect electrically coupling said n-type semiconductor region and said p-type semiconductor region with one another, said at least one thermo-electric assembly monolithically integrated on said micro-machined substrate, said thermo-electric assembly being operable to selectively perform heating and freezing processes with respect to body tissue proximal the probe after insertion of the probe into body tissue, said heating and freezing processes based on operation of said metal interconnect electrically coupling said n-type semiconductor region and said p-type semiconductor region;
   two microfluidic channels monolithically integrated in said micro-machined substrate, said two microfluidic channels separated by a gap region in said micro-machined substrate with a membrane over said gap region, said membrane extending across said two microfluidic channels with said n-type semiconductor region and said p-type semiconductor region disposed on said membrane, at least one of said two microfluidic channels being configured to direct fluid to and from a region of said micro-machined substrate proximal said thermo-electric assembly so as to confine said heating and freezing processes to said thermo-electric assembly;
   an electronics assembly configured to control said heating and freezing processes of said thermo-electric assembly;
   a temperature sensor, said sensor cooperating with said electronics assembly to provide bi-directional temperature control of said thereto-electric assembly; and
   at least one capacitive micro-machined ultrasonic transducer monolithically integrated on said micro-machined substrate, said transducer being configured to send and receive ultrasonic waves to image body tissue proximal the probe after insertion of the probe into body tissue.

8. The medical probe of claim 7, further comprising at least one electrode configured to stimulate a body tissue proximal the probe after insertion of the probe into body tissue.

9. A method of clearing plaque from a blood vessel, the method comprising:

inserting a micro-device into a blood vessel, said micro-device including a micro-machined substrate;

at least one thermo-electric assembly having a n-type semiconductor region, a p-type semiconductor region, and a metal interconnect electrically coupling said n-type semiconductor region and said p-type semiconductor region with one another, said at least one thermo-electric assembly monolithically integrated on said micro-machined substrate, said thermo-electric assembly being operable to selectively perform heating and freezing processes with respect to body tissue proximal the probe after insertion of the probe into body tissue, said heating and freezing processes based on operation of said metal interconnect electrically coupling said n-type semiconductor region and said p-type semiconductor region;

two microfluidic channels monolithically integrated in said micro-machined substrate, said two microfluidic channels separated by a gap region in said micro-machined substrate with a membrane over said gap region, said membrane extending across said two microfluidic channels with said n-type semiconductor region and said p-type semiconductor region disposed on said membrane, at least one of said two microfluidic channels being configured to direct fluid to and from a region of said micro-machined substrate proximal said thermo-electric assembly so as to confine said heating and freezing processes to said thermo-electric assembly;

an electronics assembly configured to control said heating and freezing processes of said the bi-directional assembly;

a temperature sensor, said sensor cooperating with said electronics assembly to provide bi-directional temperature control of said thermo-electric assembly; and a capacitive micro-machined ultrasonic transducer monolithically integrated on said micro-machined substrate; and operably controlling said capacitive micro-machined ultrasonic transducer to emit high frequency ultrasonic waves for breaking up plaque in said blood vessel.

10. The medical probe of claim 1, further comprising a microfluidic drug delivery channel in said micro-machined substrate, said microfluidic drug delivery channel being configured to direct fluid from a first end of said micro-machined substrate to an outlet between the first end of said micro-machined substrate and a second end of said micro-machined substrate.

11. The medical probe of claim 7, further comprising a microfluidic drug delivery channel in said micro-machined substrate, said microfluidic drug delivery channel being configured to direct fluid from a first end of said micro-machined substrate to an outlet between the first end of said micro-machined substrate and a second end of said micro-machined substrate.

12. The medical probe of claim 7, further comprising at least one microfluidic channel in said micro-machined substrate, said at least one microfluidic channel being configured to direct fluid to and from a region of said micro-machined substrate proximal said thermo-electric assembly so as to confine said heating and freezing processes to said thermo-electric assembly.

13. The medical probe of claim 12, further comprising an electronics assembly configured to control said direction of fluid to and from said region of said micro-machined substrate proximal said thermo-electric assembly via said at least one microfluidic channel.

14. A method of selectively heating and freezing body tissue, the method comprising:

inserting a probe into a body tissue, said probe including a micro-machined substrate;

at least one thermo-electric assembly having a n-type semiconductor region, a p-type semiconductor semiconductor region, and a metal interconnect electrically coupling said n-type semiconductor region and said p-type semiconductor region with one another, said at least one thermo-electric assembly monolithically integrated on said micro-machined substrate, said thermo-electric assembly being operable to selectively perform heating and freezing processes with respect to body tissue proximal the probe after insertion of the probe into body tissue, said heating and freezing processes based on operation of said metal interconnect electrically coupling said n-type semiconductor region and said p-type semiconductor region;

two microfluidic channels monolithically integrated in said micro-machined substrate, said two microfluidic channels separated by a gap region in said micro-machined substrate with a membrane over said gap region, said membrane extending across said two microfluidic channels with said n-type semiconductor region and said p-type semiconductor region disposed on said membrane;

an electronics assembly configured to control said heating and freezing processes of said thermo-electric assembly;

a temperature sensor, said sensor cooperating with said electronics assembly to provide bi-directional temperature control of said thermo-electric assembly; and a capacitive micro-machined ultrasonic transducer monolithically integrated on said micro-machined substrate and operably controlling said thermo-electric assembly to selectively heat and freeze at least one cell of said body tissue; and directing flow of fluid through at least one of said two microfluidic channels in said micro-machined substrate to a region of said micro-machined substrate proximal said thermoelectric assembly to confine said heating and freezing to said thermo-electric assembly.

15. The method of claim 14, further comprising electrically stimulating body tissue proximal the probe after insertion of the probe into said body tissue.

16. The method of claim 14, further comprising delivering a drug to body tissue via a microfluidic drug delivery channel extending from a first, proximal end of the probe to an outlet between the first end of the probe and a second, distal end of the probe.

17. The medical probe of claim 1, wherein said gap region includes a polymer.

18. The medical probe of claim 1, wherein said gap region includes a gel.

19. The medical probe of claim 1, wherein said thermo-electric assembly includes a semiconductor thermistor disposed on said membrane between said membrane and said metal interconnect.

20. The medical probe of claim 1, wherein said n-type semiconductor region is disposed at least partially over one of said two microfluidic channels and said p-type semiconductor region is disposed at least partially over the other of said two microfluidic channels, said metal interconnect disposed above said gap region between said n-type semiconductor region and said p-type semiconductor region.

\* \* \* \* \*

UNITED STATES PATENT AND TRADEMARK OFFICE
CERTIFICATE OF CORRECTION

| | | |
|---|---|---|
| PATENT NO. | : 8,454,513 B2 | Page 1 of 1 |
| APPLICATION NO. | : 11/320921 | |
| DATED | : June 4, 2013 | |
| INVENTOR(S) | : Chen et al. | |

It is certified that error appears in the above-identified patent and that said Letters Patent is hereby corrected as shown below:

On the Title page, Item (57)

In column 2, abstract, line 3, after "system" delete "configured to", therefor

In column 2, abstract, line 4, before "a", delete "the", therefor

In the Claims

In column 18, line 57, in claim 7, delete "thereto-electric" and insert --thermo-electric--, therefor In column 19, line 2, in claim 9, delete "including" and insert --including:--, therefor In column 19, line 34, in claim 9, delete "the bi-directional" and insert --thermo-electric--, therefor In column 20, line 6, in claim 14, delete "including" and insert --including:--, therefor In column 20, line 9, in claim 14, after "p-type", delete "semiconductor", therefor In column 20, line 39, in claim 14, delete "substrate" and insert --substrate;--, therefor Signed and Sealed this
Seventeenth Day of June, 2014

Michelle K. Lee
*Deputy Director of the United States Patent and Trademark Office*